United States Patent [19]

Foster

[11] Patent Number: 5,504,001
[45] Date of Patent: Apr. 2, 1996

[54] HYBRID PLASMINOGEN ACTIVATOR

[75] Inventor: Donald C. Foster, Seattle, Wash.

[73] Assignee: ZymoGenetics, Inc., Seattle, Wash.

[21] Appl. No.: 254,485

[22] Filed: Jun. 6, 1994

Related U.S. Application Data

[63] Continuation of Ser. No. 827,587, Jan. 28, 1992, abandoned, which is a continuation of Ser. No. 125,629, Nov. 25, 1987, abandoned.

[51] Int. Cl.$^6$ .............................. C12N 9/50; C12N 9/64; A61K 38/48; A61K 38/49
[52] U.S. Cl. .................. 435/219; 424/94.64; 435/226
[58] Field of Search ...................... 435/212, 216, 435/226, 219, 172.3; 424/94.64; 530/350, 327

[56] References Cited

FOREIGN PATENT DOCUMENTS 0093619  11/1983  European Pat. Off. ............... 435/212
2173804  10/1986  United Kingdom ................... 435/212

OTHER PUBLICATIONS van Zonneveld et al. PNAS 83 4670–74 (Jul. 1986).
Verstraete et al. Blood 67(6) 1529–41 (Jun. 1986).
Tamaki et al. BBA 661 280–286 (1981).
Ichimose et al. FEBS Lett. 153(2) 369–71 (Mar. 1983).

*Primary Examiner*—Richard A. Schwartz
*Assistant Examiner*—Nancy T. Vogel
*Attorney, Agent, or Firm*—Seed and Berry

[57] ABSTRACT

Hybrid proteins comprising a cross-linking domain derived from a protein that acts as an acyl-donor substrate for factor XIIIa, a fibrin-binding domain, and a serine protease domain are disclosed. Host cells transfected or transformed with an expression vector comprising a transcriptional promoter operably linked to a DNA sequence encoding such hybrid proteins are also disclosed, as well as methods for producing the proteins. The proteins may be utilized in combination with a suitable carrier or diluent as pharmaceutical compositions.

7 Claims, 21 Drawing Sheets

```
                    10                         30                        45
AAGCTTGGAT CCACC ATG GAT GCA ATG AAG AGA GGG CTC TGC TGT GTG CTG CTG CTG
                MET Asp Ala MET Lys Arg Gly Leu Cys Cys Val Leu Leu Leu
                -35                     -30
 60                    75                       90                       105
TGT GGC GCC GTC TTC GTT TCG CCC AGC CAG GAA ATC CAT GCC CGA TTC AGA AGA
Cys Gly Ala Val Phe Val Ser Pro Ser Gln Glu Ile His Ala Arg Phe Arg Arg
    -20                                         -10
        120                       135                      150                      165
GGA GCC AGA TCT TAC CAA GTG ATC TGC AGA GAT GAA AAA ACG CAG ATG ATA TAC
Gly Ala Arg Ser Tyr Gln Val Ile Cys Arg Asp Glu Lys Thr Gln MET Ile Tyr
             1                                     10
        180                       195                      210
CAG CAA CAT CAG TCA TGG CTG CGC CCT GTG CTC AGA AGC AAC CGG GTG GAA TAT
Gln Gln His Gln Ser Trp Leu Arg Pro Val Leu Arg Ser Asn Arg Val Glu Tyr
                 20                                          30
    225                       240                      255                      270
TGC TGG TGC AAC AGT GGC AGG GCA CAG TGC CAC TCA GTG CCT GTC AAA AGT TGC
Cys Trp Cys Asn Ser Gly Arg Ala Gln Cys His Ser Val Pro Val Lys Ser Cys
                     40                                                50
        285                       300                      315
AGC GAG CCA AGG TGT TTC AAC GGG GGC ACC TGC CAG CAG GCC CTG TAC TTC TCA
Ser Glu Pro Arg Cys Phe Asn Gly Gly Thr Cys Gln Gln Ala Leu Tyr Phe Ser
                              60
330                      345                      360                      375
GAT TTC GTG TGC CAG TGC CCC GAA GGA TTT GCT GGG AAG TGC TGT GAA ATA GAT
Asp Phe Val Cys Gln Cys Pro Glu Gly Phe Ala Gly Lys Cys Cys Glu Ile Asp
 70                                           80
        390                       405                      420                      435
ACC AGG GCC ACG TGC TAC GAG GAC CAG GGC ATC AGC TAC AGG GGC ACG TGG AGC
Thr Arg Ala Thr Cys Tyr Glu Asp Gln Gly Ile Ser Tyr Arg Gly Thr Trp Ser
             90                                         100
                450                      465                      480
ACA GCG GAG AGT GGC GCC GAG TGC ACC AAC TGG AAC AGC AGC GCG TTG GCC CAG
Thr Ala Glu Ser Gly Ala Glu Cys Thr Asn Trp Asn Ser Ser Ala Leu Ala Gln
                110                                         120
    495                       510                      525                      540
AAG CCC TAC AGC GGG CGG AGG CCA GAC GCC ATC AGG CTG GGC CTG GGG AAC CAC
Lys Pro Tyr Ser Gly Arg Arg Pro Asp Ala Ile Arg Leu Gly Leu Gly Asn His
                     130                                                140
            555                      570                      585
AAC TAC TGC AGA AAC CCA GAT CGA GAC TCA AAG CCC TGG TGC TAC GTC TTT AAG
Asn Tyr Cys Arg Asn Pro Asp Arg Asp Ser Lys Pro Trp Cys Tyr Val Phe Lys
                                 150
600                      615                      630                      645
GCG GGG AAG TAC AGC TCA GAG TTC TGC AGC ACC CCT GCC TGC TCT GAG GGA AAC
Ala Gly Lys Tyr Ser Ser Glu Phe Cys Ser Thr Pro Ala Cys Ser Glu Gly Asn
160                                              170
            660                      675                      690                      705
AGT GAC TGC TAC TTT GGG AAT GGG TCA GCC TAC CGT GGC ACG CAC AGC CTC ACC
Ser Asp Cys Tyr Phe Gly Asn Gly Ser Ala Tyr Arg Gly Thr His Ser Leu Thr
            180                                              190
```

*Fig. 1A*

```
         720                    735                    750
GAG TCG GGT GCC TCC TGC CTC CCG TGG AAT TCC ATG ATC CTG ATA GGC AAG GTT
Glu Ser Gly Ala Ser Cys Leu Pro Trp Asn Ser MET Ile Leu Ile Gly Lys Val
                 200                                    210
     765                    780                    795                810
TAC ACA GCA CAG AAC CCC AGT GCC CAG GCA CTG GGC CTG GGC AAA CAT AAT TAC
Tyr Thr Ala Gln Asn Pro Ser Ala Gln Ala Leu Gly Leu Gly Lys His Asn Tyr
                         220                                         230
             825                    840                    855
TGC CGG AAT CCT GAT GGG GAT GCC AAG CCC TGG TGC CAC GTG CTG AAG AAC CGC
Cys Arg Asn Pro Asp Gly Asp Ala Lys Pro Trp Cys His Val Leu Lys Asn Arg
                                 240
870                    885                    900                915
AGG CTG ACG TGG GAG TAC TGT GAT GTG CCC TCC TGC TCC ACC TGC GGC CTG AGA
Arg Leu Thr Trp Glu Tyr Cys Asp Val Pro Ser Cys Ser Thr Cys Gly Leu Arg
250                                         260
         930                    945                    960                975
CAG TAC AGC CAG CCT CAG TTT CGC ATC AAA GGA GGG CTC TTC GCC GAC ATC GCC
Gln Tyr Ser Gln Pro Gln Phe Arg Ile Lys Gly Gly Leu Phe Ala Asp Ile Ala
         270                                         280
                 990                   1005                   1020
TCC CAC CCC TGG CAG GCT GCC ATC TTT GCC AAG CAC AGG AGG TCG CCC GGA GAG
Ser His Pro Trp Gln Ala Ala Ile Phe Ala Lys His Arg Arg Ser Pro Gly Glu
                         290                                         300
        1035                   1050                   1065                   1080
CGG TTC CTG TGC GGG GGC ATA CTC ATC AGC TCC TGC TGG ATT CTC TCT GCC GCC
Arg Phe Leu Cys Gly Gly Ile Leu Ile Ser Ser Cys Trp Ile Leu Ser Ala Ala
                                 310                                         320
             1095                   1110                   1125
CAC TGC TTC CAG GAG AGG TTT CCG CCC CAC CAC CTG ACG GTG ATC TTG GGC AGA
His Cys Phe Gln Glu Arg Phe Pro Pro His His Leu Thr Val Ile Leu Gly Arg
                                         330
1140                   1155                   1170                   1185
ACA TAC CGG GTG GTC CCT GGC GAG GAG GAG CAG AAA TTT GAA GTC GAA AAA TAC
Thr Tyr Arg Val Val Pro Gly Glu Glu Glu Gln Lys Phe Glu Val Glu Lys Tyr
340                                         350
         1200                   1215                   1230                   1245
ATT GTC CAT AAG GAA TTC GAT GAT GAC ACT TAC GAC AAT GAC ATT GCG CTG CTG
Ile Val His Lys Glu Phe Asp Asp Asp Thr Tyr Asp Asn Asp Ile Ala Leu Leu
                 360                                         370
                     1260                   1275                   1290
CAG CTG AAA TCG GAT TCG TCC CGC TGT GCC CAG GAG AGC AGC GTG GTC CGC ACT
Gln Leu Lys Ser Asp Ser Ser Arg Cys Ala Gln Glu Ser Ser Val Val Arg Thr
                             380                                         390
         1305                   1320                   1335                   1350
GTG TGC CTT CCC CCG GCG GAC CTG CAG CTG CCG GAC TGG ACG GAG TGT GAG CTC
Val Cys Leu Pro Pro Ala Asp Leu Gln Leu Pro Asp Trp Thr Glu Cys Glu Leu
                                 400                                         410
                 1365                   1380                   1395
TCC GGC TAC GGC AAG CAT GAG GCC TTG TCT CCT TTC TAT TCG GAG CGG CTG AAG
Ser Gly Tyr Gly Lys His Glu Ala Leu Ser Pro Phe Tyr Ser Glu Arg Leu Lys
                                         420
```

*Fig. 1B*

```
1410                1425                 1440                1455
GAG GCT CAT GTC AGA CTG TAC CCA TCC AGC CGC TGC ACA TCA CAA CAT TTA CTT
Glu Ala His Val Arg Leu Tyr Pro Ser Ser Arg Cys Thr Ser Gln His Leu Leu
430                                      440
          1470                 1485                 1500                1515
AAC AGA ACA GTC ACC GAC AAC ATG CTG TGT GCT GGA GAC ACT CGG AGC GGC GGG
Asn Arg Thr Val Thr Asp Asn MET Leu Cys Ala Gly Asp Thr Arg Ser Gly Gly
         450                                       460
         1530                1545                 1560
CCC CAG GCA AAC TTG CAC GAC GCC TGC CAG GGC GAT TCG GGA GGC CCC CTG GTG
Pro Gln Ala Asn Leu His Asp Ala Cys Gln Gly Asp Ser Gly Gly Pro Leu Val
                  470                                       480
      1575                 1590                1605                1620
TGT CTG AAC GAT GGC CGC ATG ACT TTG GTG GGC ATC ATC AGC TGG GGC CTG GGC
Cys Leu Asn Asp Gly Arg MET Thr Leu Val Gly Ile Ile Ser Trp Gly Leu Gly
                           490                                      500
         1635                1650                1665
TGT GGA CAG AAG GAT GTC CCG GGT GTG TAC ACC AAG GTT ACC AAC TAC CTA GAC
Cys Gly Gln Lys Asp Val Pro Gly Val Tyr Thr Lys Val Thr Asn Tyr Leu Asp
                                    510
1680                 1695                   1714        1724       1734
TGG ATT CGT GAC AAC ATG CGA CCG TGA CCAGGAACAC CCGACTCCTC AAAAGCAAAT GAGATC
Trp Ile Arg Asp Asn MET Arg Pro
520                          527
```

*Fig. 1C*

```
Lys Thr Lys Asn Gly Ile Thr Cys Gln Lys Trp Ser Ser Thr Ser Pro His Arg Pro Arg
AAG ACC AAA AAC GGT ATT ACA TGT CAG AAA TGG TCA TCT ACT AGT CCA CAC CGG CCG CGG

Phe Ser Pro Ala Thr His Pro Ser Glu Gly Leu Glu Glu Asn Tyr Cys Arg Asn Pro Asp
TTT TCT CCA GCT ACC CAT CCA TCT GAA GGC CTG GAA GAG AAT TAC TGT AGG AAT CCA GAT

Asn Asp Pro Gln Gly Pro Trp Cys Tyr Thr Thr Asp Pro Glu Lys Arg Tyr Asp Tyr Cys
AAC GAT CCT CAG GGT CCC TGG TGT TAC ACC ACA GAC CCC GAG AAG AGG TAC GAC TAC TGC

Asp Ile Leu Glu Cys
GAT ATC CTG GAA TGC
```

*Fig. 4*

```
        -35                    -30                                           -20
Met Asp Ala Met Lys Arg Gly Leu Cys Cys Val Leu Leu Leu Cys Gly Ala Val Phe Val
ATG GAT GCA ATG AAG AGA GGG CTC TGC TGT GTG CTG CTG CTG TGT GGC GCC GTC TTC GTT

-10                                      -1  +1
Ser Pro Ser Gln Glu Ile His Ala Arg Phe Arg Arg Gly Ala Arg Ser Tyr Gln Val Ile
TCG CCC AGC CAG GAA ATC CAT GCC CGA TTC AGA AGA GGA GCC AGA TCT TAC CAA GTG ATC 10                                    20
Cys Arg Asp Glu Lys Thr Gln Met Ile Tyr Gln Gln His Gln Ser Trp Leu Arg Pro Val
TGC AGA GAT GAA AAA ACG CAG ATG ATA TAC CAG CAA CAT CAG TCA TGG CTG CGC CCT GTG 30                                    40
Leu Arg Ser Asn Arg Val Glu Tyr Cys Trp Cys Asn Ser Gly Arg Ala Gln Cys His Ser
CTC AGA AGC AAC CGG GTG GAA TAT TGC TGG TGC AAC AGT GGC AGG GCA CAG TGC CAC TCA 50                                    60
Val Pro Val Lys Ser Cys Ser Glu Pro Arg Cys Phe Asn Gly Gly Thr Cys Gln Gln Ala
GTG CCT GTC AAA AGT TGC AGC GAG CCA AGG TGT TTC AAC GGG GGC ACC TGC CAG CAG GCC 70                                    80
Leu Tyr Phe Ser Asp Phe Val Cys Gln Cys Pro Glu Gly Phe Ala Gly Lys Cys Cys Glu
CTG TAC TTC TCA GAT TTC GTG TGC CAG TGC CCC GAA GGA TTT GCT GGG AAG TGC TGT GAA 90                                    100
Ile Asp Thr Arg Ala Thr Cys Lys Thr Gly Asp Gly Lys Asn Tyr Arg Gly Thr Met Ser
ATA GAT ACG CGT GCC ACG TGC AAG ACC GGT GAT GGT AAA AAC TAC CGA GGT ACC ATG TCC 110                                   120
Lys Thr Lys Asn Gly Ile Thr Cys Gln Lys Trp Ser Ser Thr Ser Pro His Arg Pro Arg
AAG ACC AAA AAC GGT ATT ACA TGT CAG AAA TGG TCA TCT ACT AGT CCA CAC CGG CCG CGG 130                                   140
Phe Ser Pro Ala Thr His Pro Ser Glu Gly Leu Glu Glu Asn Tyr Cys Arg Asn Pro Asp
TTT TCT CCA GCT ACC CAT CCA TCT GAA GGC CTG GAA GAG AAT TAC TGT AGG AAT CCA GAT 150                                   160
Asn Asp Pro Gln Gly Pro Trp Cys Tyr Thr Thr Asp Pro Glu Lys Arg Tyr Asp Tyr Cys
AAC GAT CCT CAG GGT CCC TGG TGT TAC ACC ACA GAC CCC GAG AAG AGG TAC GAC TAC TGC 170                                   180
Asp Ile Leu Glu Cys Ser Glu Gly Asn Ser Asp Cys Tyr Phe Gly Asn Gly Ser Ala Tyr
GAT ATC CTG GAA TGC TCT GAG GGA AAC AGT GAC TGC TAC TTT GGG AAT GGG TCA GCC TAC 190                                   200
Arg Gly Thr His Ser Leu Thr Glu Ser Gly Ala Ser Cys Leu Pro Trp Asn Ser Met Ile
CGT GGC ACG CAC AGC CTC ACC GAG TCG GGT GCC TCC TGC CTC CCG TGG AAT TCC ATG ATC 210                                   220
Leu Ile Gly Lys Val Tyr Thr Ala Gln Asn Pro Ser Ala Gln Ala Leu Gly Leu Gly Lys
CTG ATA GGC AAG GTT TAC ACA GCA CAG AAC CCC AGT GCC CAG GCA CTG GGC CTG GGC AAA
```

*Fig. 10A*

```
                      230                                                  240
His Asn Tyr Cys Arg Asn Pro Asp Gly Asp Ala Lys Pro Trp Cys His Val Leu Lys Asn
CAT AAT TAC TGC CGG AAT CCT GAT GGG GAT GCC AAG CCC TGG TGC CAC GTG CTG AAG AAC 250                                                  260
Arg Arg Leu Thr Trp Glu Tyr Cys Asp Val Pro Ser Cys Ser Thr Cys Gly Leu Arg Gln
CGC AGG CTG ACG TGG GAG TAC TGT GAT GTG CCC TCC TGC TCC ACC TGC GGC CTG AGA CAG 270                                                  280
Tyr Ser Gln Pro Gln Phe Arg Ile Lys Gly Gly Leu Phe Ala Asp Ile Ala Ser His Pro
TAC AGC CAG CCT CAG TTT CGC ATC AAA GGA GGG CTC TTC GCC GAC ATC GCC TCC CAC CCC 290                                                  300
Trp Gln Ala Ala Ile Phe Ala Lys His Arg Arg Ser Pro Gly Glu Arg Phe Leu Cys Gly
TGG CAG GCT GCC ATC TTT GCC AAG CAC AGG AGG TCG CCC GGA GAG CGG TTC CTG TGC GGG 310                                                  320
Gly Ile Leu Ile Ser Ser Cys Trp Ile Leu Ser Ala Ala His Cys Phe Gln Glu Arg Phe
GGC ATA CTC ATC AGC TCC TGC TGG ATT CTC TCT GCC GCC CAC TGC TTC CAG GAG AGG TTT 330                                                  340
Pro Pro His His Leu Thr Val Ile Leu Gly Arg Thr Tyr Arg Val Val Pro Gly Glu Glu
CCG CCC CAC CAC CTG ACG GTG ATC TTG GGC AGA ACA TAC CGG GTG GTC CCT GGC GAG GAG 350                                                  360
Glu Gln Lys Phe Glu Val Glu Lys Tyr Ile Val His Lys Glu Phe Asp Asp Asp Thr Tyr
GAG CAG AAA TTT GAA GTC GAA AAA TAC ATT GTC CAT AAG GAA TTC GAT GAT GAC ACT TAC 370                                                  380
Asp Asn Asp Ile Ala Leu Leu Gln Leu Lys Ser Asp Ser Ser Arg Cys Ala Gln Glu Ser
GAC AAT GAC ATT GCG CTG CTG CAG CTG AAA TCG GAT TCG TCC CGC TGT GCC CAG GAG AGC 390                                                  400
Ser Val Val Arg Thr Val Cys Leu Pro Pro Ala Asp Leu Gln Leu Pro Asp Trp Thr Glu
AGC GTG GTC CGC ACT GTG TGC CTT CCC CCG GCG GAC CTG CAG CTG CCG GAC TGG ACG GAG 410                                                  420
Cys Glu Leu Ser Gly Tyr Gly Lys His Glu Ala Leu Ser Pro Phe Tyr Ser Glu Arg Leu
TGT GAG CTC TCC GGC TAC GGC AAG CAT GAG GCC TTG TCT CCT TTC TAT TCG GAG CGG CTG 430                                                  440
Lys Glu Ala His Val Arg Leu Tyr Pro Ser Ser Arg Cys Thr Ser Gln His Leu Leu Asn
AAG GAG GCT CAT GTC AGA CTG TAC CCA TCC AGC CGC TGC ACA TCA CAA CAT TTA CTT AAC 450                                                  460
Arg Thr Val Thr Asp Asn Met Leu Cys Ala Gly Asp Thr Arg Ser Gly Gly Pro Gln Ala
AGA ACA GTC ACC GAC AAC ATG CTG TGT GCT GGA GAC ACT CGG AGC GGC GGG CCC CAG GCA 470                                                  480
Asn Leu His Asp Ala Cys Gln Gly Asp Ser Gly Gly Pro Leu Val Cys Leu Asn Asp Gly
AAC TTG CAC GAC GCC TGC CAG GGC GAT TCG GGA GGC CCC CTG GTG TGT CTG AAC GAT GGC
```

*Fig. 10B*

```
              490                                              500
Arg Met Thr Leu Val Gly Ile Ile Ser Trp Gly Leu Gly Cys Gly Gln Lys Asp Val Pro
CGC ATG ACT TTG GTG GGC ATC ATC AGC TGG GGC CTG GGC TGT GGA CAG AAG GAT GTC CCG 510                                              520        524
Gly Val Tyr Thr Lys Val Thr Asn Tyr Leu Asp Trp Ile Arg Asp Asn Met Arg Pro ---
GGT GTG TAC ACA AAG GTT ACC AAC TAC CTA GAC TGG ATT CGT GAC AAC ATG CGA CCG TGA
```

*Fig. 10C*

```
-35                    -30                                              -20
Met Asp Ala Met Lys Arg Gly Leu Cys Cys Val Leu Leu Leu Cys Gly Ala Val Phe Val
ATG GAT GCA ATG AAG AGA GGG CTC TGC TGT GTG CTG CTG CTG TGT GGC GCC GTC TTC GTT

-10                                         -1  +1
Ser Pro Ser Gln Glu Ile His Ala Arg Phe Arg Arg Gly Ala Arg Ser Tyr Gln Val Ile
TCG CCC AGC CAG GAA ATC CAT GCC CGA TTC AGA AGA GGA GCC AGA TCT TAC CAA GTG ATC 10                                          20
Cys Arg Asp Glu Lys Thr Gln Met Ile Tyr Gln Gln His Gln Ser Trp Leu Arg Pro Val
TGC AGA GAT GAA AAA ACG CAG ATG ATA TAC CAG CAA CAT CAG TCA TGG CTG CGC CCT GTG 30                                          40
Leu Arg Ser Asn Arg Val Glu Tyr Cys Trp Cys Asn Ser Gly Arg Ala Gln Cys His Ser
CTC AGA AGC AAC CGG GTG GAA TAT TGC TGG TGC AAC AGT GGC AGG GCA CAG TGC CAC TCA 50                                          60
Val Pro Val Lys Ser Cys Ser Glu Pro Arg Cys Phe Asn Gly Gly Thr Cys Gln Gln Ala
GTG CCT GTC AAA AGT TGC AGC GAG CCA AGG TGT TTC AAC GGG GGC ACC TGC CAG CAG GCC 70                                          80
Leu Tyr Phe Ser Asp Phe Val Cys Gln Cys Pro Glu Gly Phe Ala Gly Lys Cys Cys Glu
CTG TAC TTC TCA GAT TTC GTG TGC CAG TGC CCC GAA GGA TTT GCT GGG AAG TGC TGT GAA 90                                         100
Ile Asp Thr Arg Ala Thr Cys Lys Thr Gly Asn Gly Lys Asn Tyr Arg Gly Thr Met Ser
ATA GAT ACG CGT GCC ACG TGC AAG ACC GGT AAT GGT AAA AAC TAC CGA GGT ACC ATG TCC 110                                         120
Lys Thr Lys Asn Gly Ile Thr Cys Gln Lys Trp Ser Ser Thr Ser Pro His Arg Pro Arg
AAG ACC AAA AAC GGT ATT ACA TGT CAG AAA TGG TCA TCT ACT AGT CCA CAC CGG CCG CGG 130                                         140
Phe Ser Pro Ala Thr His Pro Ser Glu Gly Leu Glu Glu Asn Tyr Cys Arg Asn Pro Asp
TTT TCT CCA GCT ACC CAT CCA TCT GAA GGC CTG GAA GAG AAT TAC TGT AGG AAT CCA GAT 150                                         160
Asn Asp Pro Gln Gly Pro Trp Cys Tyr Thr Thr Asp Pro Glu Lys Arg Tyr Asp Tyr Cys
AAC GAT CCT CAG GGT CCC TGG TGT TAC ACC ACA GAC CCC GAG AAG AGG TAC GAC TAC TGC 170                                         180
Asp Ile Leu Glu Cys Ser Glu Gly Asn Ser Asp Cys Tyr Phe Gly Asn Gly Ser Ala Tyr
GAT ATC CTG GAA TGC TCT GAG GGA AAC AGT GAC TGC TAC TTT GGG AAT GGG TCA GCC TAC 190                                         200
Arg Gly Thr His Ser Leu Thr Glu Ser Gly Ala Ser Cys Leu Pro Trp Asn Ser Met Ile
CGT GGC ACG CAC AGC CTC ACC GAG TCG GGT GCC TCC TGC CTC CCG TGG AAT TCC ATG ATC 210                                         220
Leu Ile Gly Lys Val Tyr Thr Ala Gln Asn Pro Ser Ala Gln Ala Leu Gly Leu Gly Lys
CTG ATA GGC AAG GTT TAC ACA GCA CAG AAC CCC AGT GCC CAG GCA CTG GGC CTG GGC AAA
```

*Fig. 11A*

```
                    230                                          240
His Asn Tyr Cys Arg Asn Pro Asp Gly Asp Ala Lys Pro Trp Cys His Val Leu Lys Asn
CAT AAT TAC TGC CGG AAT CCT GAT GGG GAT GCC AAG CCC TGG TGC CAC GTG CTG AAG AAC 250                                          260
Arg Arg Leu Thr Trp Glu Tyr Cys Asp Val Pro Ser Cys Ser Thr Cys Gly Leu Arg Gln
CGC AGG CTG ACG TGG GAG TAC TGT GAT GTG CCC TCC TGC TCC ACC TGC GGC CTG AGA CAG 270                                          280
Tyr Ser Gln Pro Gln Phe Arg Ile Lys Gly Gly Leu Phe Ala Asp Ile Ala Ser His Pro
TAC AGC CAG CCT CAG TTT CGC ATC AAA GGA GGG CTC TTC GCC GAC ATC GCC TCC CAC CCC 290                                          300
Trp Gln Ala Ala Ile Phe Ala Lys His Arg Arg Ser Pro Gly Glu Arg Phe Leu Cys Gly
TGG CAG GCT GCC ATC TTT GCC AAG CAC AGG AGG TCG CCC GGA GAG CGG TTC CTG TGC GGG 310                                          320
Gly Ile Leu Ile Ser Ser Cys Trp Ile Leu Ser Ala Ala His Cys Phe Gln Glu Arg Phe
GGC ATA CTC ATC AGC TCC TGC TGG ATT CTC TCT GCC GCC CAC TGC TTC CAG GAG AGG TTT 330                                          340
Pro Pro His His Leu Thr Val Ile Leu Gly Arg Thr Tyr Arg Val Val Pro Gly Glu Glu
CCG CCC CAC CAC CTG ACG GTG ATC TTG GGC AGA ACA TAC CGG GTG GTC CCT GGC GAG GAG 350                                          360
Glu Gln Lys Phe Glu Val Glu Lys Tyr Ile Val His Lys Glu Phe Asp Asp Asp Thr Tyr
GAG CAG AAA TTT GAA GTC GAA AAA TAC ATT GTC CAT AAG GAA TTC GAT GAT GAC ACT TAC 370                                          380
Asp Asn Asp Ile Ala Leu Leu Gln Leu Lys Ser Asp Ser Ser Arg Cys Ala Gln Glu Ser
GAC AAT GAC ATT GCG CTG CTG CAG CTG AAA TCG GAT TCG TCC CGC TGT GCC CAG GAG AGC 390                                          400
Ser Val Val Arg Thr Val Cys Leu Pro Pro Ala Asp Leu Gln Leu Pro Asp Trp Thr Glu
AGC GTG GTC CGC ACT GTG TGC CTT CCC CCG GCG GAC CTG CAG CTG CCG GAC TGG ACG GAG 410                                          420
Cys Glu Leu Ser Gly Tyr Gly Lys His Glu Ala Leu Ser Pro Phe Tyr Ser Glu Arg Leu
TGT GAG CTC TCC GGC TAC GGC AAG CAT GAG GCC TTG TCT CCT TTC TAT TCG GAG CGG CTG 430                                          440
Lys Glu Ala His Val Arg Leu Tyr Pro Ser Ser Arg Cys Thr Ser Gln His Leu Leu Asn
AAG GAG GCT CAT GTC AGA CTG TAC CCA TCC AGC CGC TGC ACA TCA CAA CAT TTA CTT AAC 450                                          460
Arg Thr Val Thr Asp Asn Met Leu Cys Ala Gly Asp Thr Arg Ser Gly Gly Pro Gln Ala
AGA ACA GTC ACC GAC AAC ATG CTG TGT GCT GGA GAC ACT CGG AGC GGC GGG CCC CAG GCA 470                                          480
Asn Leu His Asp Ala Cys Gln Gly Asp Ser Gly Gly Pro Leu Val Cys Leu Asn Asp Gly
AAC TTG CAC GAC GCC TGC CAG GGC GAT TCG GGA GGC CCC CTG GTG TGT CTG AAC GAT GGC
```

*Fig. 11B*

```
                490                                              500
Arg Met Thr Leu Val Gly Ile Ile Ser Trp Gly Leu Gly Cys Gly Gln Lys Asp Val Pro
CGC ATG ACT TTG GTG GGC ATC ATC AGC TGG GGC CTG GGC TGT GGA CAG AAG GAT GTC CCG 510                                              520         524
Gly Val Tyr Thr Lys Val Thr Asn Tyr Leu Asp Trp Ile Arg Asp Asn Met Arg Pro ---
GGT GTG TAC ACA AAG GTT ACC AAC TAC CTA GAC TGG ATT CGT GAC AAC ATG CGA CCG TGA
```

*Fig. 11C*

| | |
|---|---|
| 19A | CRDEKTQMIYQQHQSWLRPVLRSNRVEYCWCNSGRAQC |
| 19B | CFDNGKSYKIGETWERPYEGFMLSCTCLGNGREFRC |
| 19C | CHDEKTGSSYKIGEQWERPYLSGNRLECTCLGNGSGRWQC |
| 19D | CFDNGKSYKIGETWERPYEGFMLSCTCLGNGSGRWQC |
| 19E | CFDNGKSYKIGEQWERPYLSGNRLECTCLGNGREFRC |
| 19F | CFDNGKSYKIGEQWERPYLSGNRLECTCLGNGSGRWQC |
| 19G | CHDEKTGSSYKIGETWERPYEGFMLSCTCLGNGSGRWQC |
| 19H | CHDEKTGSSYKIGEQWERPYLSGNRLECTCLGNGRGEFRC |
| 19I | CHDEKTGSSYKIGETWERPYEGFMLSCTCLGNGRGEFRC |

*Fig. 12*

FRAGMENT "A"

```
         KpnI                                                    NsiI
          |                                                       |
     SerValProValLysSerCysSerGluProArgCysPheAsnGlyGlyThrCysMETGluGlyAsnHis
  1  TCGGTACCTGTTAAATCTTGTTCTGAACCTAGATGTTTTAATGGAGGAACATGCATGGAAGGAAATCAT  69
     AGCCATGGACAATTTAGAACAAGACTTGGATCTACAAAATTACCTCCTTGTACGTACCTTCCTTTAGTA
         8
                                                                  XhoI
                                                                   |
     LeuAlaAsnPheValCysGlnCysProGluGlyPheAlaGlyLysSerCysGluIleAspThrArgAla
 70  CTTGCTAATTTTGTTTGTCAATGTCCTGAAGGATTTGCTGGAAAATCTTGTGAAATTGATACTCGAGCT  138
     GAACGATTAAAACAAACAGTTACAGGACTTCCTAAACGACCTTTTAGAACACTTTAACTATGAGCTCGA
                                                                      132
```

FRAGMENT "B"

```
         KpnI
          |
     SerValProValLysSerCysGluSerAsnProCysLeuAsnGlyGlySerCysLysAspAspIleAsn
  1  TCGGTACCTGTTAAATCTTGTGAATCTAATCCTTGTCTTAATGGAGGATCTTGTAAAGATGATATTAAT  69
     AGCCATGGACAATTTAGAACACTTAGATTAGGAACAGAATTACCTCCTAGAACATTTCTACTATAATTA
         8
         NdeI                                                    XhoI
          |                                                       |
     SerTyrGluCysTrpCysProPheGlyPheGluGlyLysAsnCysGluIleAspThrArgAla
 70  TCATATGAATGTTGGTGTCCTTTTGGATTTGAAGGAAAAAATTGTGAAATTGATACTCGAGCT  132
     AGTATACTTACAACCACAGGAAAACCTAAACTTCCTTTTTTAACACTTTAACTATGAGCTCGA
         73                                                       126
```

FRAGMENT "C"

```
         KpnI
          |
     SerValProValLysSerCysGluSerAsnProCysLeuAsnGlyGlyThrCysGlnGlnAlaLeuTyr
  1  TCGGTACCTGTTAAATCTTGTGAATCTAATCCTTGTCTTAATGGAGGAACATGTCAACAAGCTCTTTAT  69
     AGCCATGGACAATTTAGAACACTTAGATTAGGAACAGAATTACCTCCTTGTACAGTTGTTCGAGAAATA
         8
                                                                  XhoI
                                                                   |
     PheSerAspPheValCysGlnCysProGluGlyPheAlaGlyLysSerCysGluIleAspThrArgAla
 70  TTTTCTGATTTTGTTTGTCAATGTCCTGAAGGATTTGCTGGAAAATCTTGTGAAATTGATACTCGAGCT  138
     AAAAGACTAAAACAAACAGTTACAGGACTTCCTAAACGACCTTTTAGAACACTTTAACTATGAGCTCGA
                                                                      132
```

FRAGMENT "D"

```
         KpnI                                                    NsiI
          |                                                       |
     SerValProValLysSerCysGluSerAsnProCysLeuAsnGlyGlyThrCysMETGluGlyAsnHis
  1  TCGGTACCTGTTAAATCTTGTGAATCTAATCCTTGTCTTAATGGAGGAACATGCATGGAAGGAAATCAT  69
     AGCCATGGACAATTTAGAACACTTAGATTAGGAACAGAATTACCTCCTTGTACGTACCTTCCTTTAGTA
         8
                                                                  XhoI
                                                                   |
     LeuAlaAsnPheValCysGlnCysProGluGlyPheAlaGlyLysSerCysGluIleAspThrArgAla
 70  CTTGCTAATTTTGTTTGTCAATGTCCTGAAGGATTTGCTGGAAAATCTTGTGAAATTGATACTCGAGCT  138
     GAACGATTAAAACAAACAGTTACAGGACTTCCTAAACGACCTTTTAGAACACTTTAACTATGAGCTCGA
                                                                      132
```

*Fig. 15*

```
1                             10                              15
Ser-Asn-Gln-Glu-Gln-Val-Ser-Pro-Leu-Thr-Gly-Leu-Lys-Lys-Gly-Ser-t-PA
```

*Fig. 16*

HYBRID PLASMINOGEN ACTIVATOR

CROSS-REFERENCE TO RELATED APPLICATION

This application is a continuation of U.S. patent application Ser. No. 07/827,587, filed Jan. 28, 1992, now abandoned, which is a continuation of U.S. Ser. No. 07/125,629, filed Nov. 25, 1987, now abandoned.

TECHNICAL FIELD

The present invention relates to fibrinolytic factors in general, methods for producing them and pharmaceutical and diagnostic compositions containing them. More specifically, the invention relates to hybrid proteins comprising portions of tissue plasminogen activator and a protein which acts as an acyl donor substrate in a factor XIIIa-catalyzed cross-linking reaction.

BACKGROUND ART

Hemostasis is maintained by a complex interplay of a variety of enzymes. Clotting factors interact in a "cascade" of activation steps which eventually leads to the formation of a fibrin clot. Subsequent degradation of the fibrin clot is accomplished by the fibrinolytic system, which involves the serine protease plasmin, a proteolytic enzyme which breaks down fibrin plasmin is a broad spectrum protease which also cleaves certain coagulation factors, thereby inactivating them. Production of plasmin from its inactive precursor, plasminogen, is mediated by tissue plasminogen activator (t-PA), itself a serine protease. The proteolytic activity of plasmin on fibrin clots is inhibited by $\alpha_2$-plasmin inhibitor ($\alpha_2$-PI). $\alpha_2$-PI is covalently attached to the fibrin matrix through the action of factor XIIIa, a clot stabilizing enzyme (Sakata and Aoki, *J. Clin Invest.* 69:536–542, 1981; Tamaki and Aoki, *Biochem. Biophys Acta* 661:280–286, 1981; Aoki et al., *J. Clin Invest.* 63:877–884, 1979; and Tamaki and Aoki, J. Biol. Chem. 257:14767–14772, 1982).

If the normal hemostatic system becomes upset, clots may form at inappropriate times and places, leading to myocardial infarction, deep vein thrombosis, pulmonary embolism and stroke. Tissue damage resulting from these conditions may result in death or serious disability.

Tissue damage does not occur immediately upon obstruction of the blood supply to tissues, but develops over several hours after the initial stoppage of blood flow. Accordingly, the use of fibrinolytic agents to restore blood flow and minimize damage is of great clinical interest.

Three fibrinolytic agents are now in use. These are streptokinase, a bacterial protein; urokinase, a serine protease originally found in human urine; and tissue plasminogen activator, the natural activator of plasminogen. Streptokinase is an activator of plasminogen, able to convert the zymogen to its active form throughout the body. This may lead to non-specific plasminogen activation and to disruption of the hemostatic system as coagulation factors are degraded. Furthermore, streptokinase is a foreign protein and may therefore elicit an immune response in patients receiving it. Urokinase, although a human protein, is also not specific for activity at the site of the clot. Tissue plasminogen activator has been viewed as the preferred agent for fibrinolytic therapy because it is the normal vascular activator of plasminogen and because its activity is stimulated in the presence of fibrin. Early studies indicated that therapeutic administration of t-PA could result in lysis of undesirable clots without the systemic effects seen with streptokinase and urokinase. However, as will be discussed below, native t-PA has not fulfilled these expectations in clinical trials.

t-PA normally circulates in the blood as a single polypeptide chain of Mr=72,000 daltons which is converted to a two chain form by cleavage of a peptide bond between amino acids 275 (Arg) and 276 (Ile) (numbering of t-PA amino acids is shown in FIG. 1). The heavy chain of t-PA (two variants of Mr 40,000 and 37,000) is derived from the amino terminus of the protein and is responsible for the binding of t-PA to fibrin, while the light chain (Mr 33,000) is derived from the carboxy-terminal end of the molecule and contains the serine protease domain. The structure of t-PA is reviewed by Ny et al. (*Proc. Natl. Acad. Sci. USA* 81:5355–5359, 1984.) Cleavage to the two chain form is catalyzed by trypsin or plasmin, and is accompanied by an increase in activity as measured using synthetic substrates, and by an increase in fibrin-independent proteolytic activity. Binding of t-PA to fibrin facilitates this cleavage. t-PA binds to fibrin in a non-covalent manner at two sites in the heavy chain of the activator. The finger domain and the kringle 2 domain bind to fibrin with high affinity (van Zonneveld et al., *J. Biol. Chem.* 261:14212, 1986). Binding at the kringle 2 domain occurs via a lysine binding site on that structure.

The single chain form of t-PA is essentially inactive in the absence of fibrin. However, once it is converted to the two chain form, it also possesses considerable proteolytic activity in the absence of polymerized fibrin and may circulate through the blood stream and activate plasminogen in a nonspecific manner. This effect becomes significant in a clinical situation where doses of t-PA far greater than normal physiological levels must be administered. The short plasma half-life of t-PA and the presence of circulating t-PA inhibitors add to the need for large doses. In practice, then, it has been found that t-PA shares many of the undesirable side effects of streptokinase and urokinase.

Various researchers have attempted to alter t-PA to increase its fibrin affinity or specificity. Rosa and Rosa (published PCT application WO 86/01538) modified the Lys at position 277 of native t-PA to stabilize the single chain form of the molecule. Heyneker and Vehar (published UK patent application 2,173,804) produced variant forms of t-PA having amino acid substitutions around the cleavage site. Van Zonneveld et al. (*Proc. Natl. Acad. Sci. USA* 83:4670–4674, 1986) and Robinson et al. (EP 207,589) disclose mutant forms of t-PA in which portions of the heavy chain have been deleted. Hung et al. (published UK patent application 2,179,948) disclose plasminogen activators containing plural, heterologous kringle domains. Haigwood et al. (EP 227,462) mutagenized t-PA at several sites in an effort to improve its properties. These variant forms of t-PA do not fully overcome the problems associated with the native molecule, nor has their efficacy been demonstrated in a clinical setting.

There remains a need in the art for a plasminogen activating protein with an enhanced affinity for fibrin and a consequent increase in clot lysing specificity. The present invention fulfills this need by providing novel hybrid proteins derived from tissue plasminogen activator and a protein which can be cross-linked to fibrin by factor XIIIa. A particularly preferred such protein is $\alpha_2$-plasmin inhibitor. These hybrid proteins have an increased affinity for fibrin due to their ability to be covalently cross-linked to fibrin by factor XIIIa. The resulting increase in specificity leads to a reduction of systemic bleeding effects and greater clinical suitability. The hybrid proteins can be used to lyse existing clots in heart attack and stroke victims and in others where specific clot lysis is therapeutically desirable. In addition, they may be used as diagnostic agents for imaging blood clots.

DISCLOSURE OF THE INVENTION

Briefly stated, the present invention discloses a series of hybrid proteins comprising a cross-linking domain derived from a protein that acts as an acyl-donor substrate for factor XIIIa, a fibrin-binding domain, and a serine protease domain. The cross-linking domain may be derived from a protein such as $\alpha_2$-plasmin inhibitor, thrombospondin, β-casein, $\alpha_2$-macroglobulin, collagen or factor V. In a preferred embodiment, the cross-linking domain is derived from $\alpha_2$-plasmin inhibitor. Within a particularly preferred embodiment, the cross-linking domain comprises the amino-terminal twelve amino acids of $\alpha_2$-plasmin inhibitor. Within a preferred embodiment, the fibrin-binding domain is substantially the heavy chain of native t-PA and the serine protease domain is substantially the light chain of native t-PA, the protein having increased resistance to cleavage by plasmin as compared to native t-PA. The serine protease domain may also be substantially the heavy chain of urokinase. The fibrin-binding domain may comprise the growth factor region of native t-PA, or a growth factor region derived from FVII, FIX, protein C or epidermal growth factor. Alternatively, the fibrin-binding domain may comprise at least one finger region having an amino acid sequence selected from the group consisting of the sequences set forth in FIGS. 12(A)–(I), or a growth factor region comprising an amino acid sequence selected from the group consisting of fragment A, fragment B, fragment C and fragment D, as shown in FIG. 15. In addition, the fibrin-binding domain may contain at least one kringle structure, for instance, the K1, K4 or K5 kringles of plasminogen. The fibrin-binding domain may also contain two kringle structures, at least one of which lacks carbohydrate.

In another aspect of the present invention, an expression vector comprising a transcriptional promoter operably linked to a DNA sequence encoding a plasminogen activator is disclosed. The plasminogen activator comprises a cross-linking domain derived from a protein that acts as an acyl-donor substrate for factor XIIIa, a fibrin-binding domain, and a serine protease domain. Suitable cross-linking domains, fibrin-binding domains, and serine protease domains include the respective domains discussed above.

In yet another aspect of the present invention, host cells transfected or transformed with an expression vector comprising a transcriptional promoter operably linked to a DNA sequence encoding such a plasminogen activator are disclosed. The host cells may be mammalian host cells, such as tk–BHK cells.

In a related aspect of the present invention, a method for producing a plasminogen activator is disclosed, comprising the steps of (a) transfecting host cells with an expression vector comprising a transcriptional promoter operably linked to a DNA sequence encoding a plasminogen activator as set forth above; (b) growing the host cells in an appropriate medium; and (c) isolating the protein product of the DNA sequence from the host cells.

Within another aspect of the present invention, a pharmaceutical composition comprising a plasminogen activator comprising a cross-linking domain derived from a protein that acts as an acyl-donor substrate for factor XIIIa, a fibrin-binding domain, and a serine protease domain, in combination with a physiologically acceptable carrier or diluent is disclosed. Suitable carriers or diluents include sterile water or sterile saline.

These and other aspects of the present invention will become evident upon reference to the following detailed description and attached drawings.

BRIEF DESCRIPTION OF THE DRAWINGS

FIGS. 1a–1g illustrate the pre-pro t-PA coding sequence constructed from cDNA and synthesized oligonucleotides as described herein, together with the amino acid sequence of the encoded protein. Numbers above the lines refer to nucleotide position and numbers below the lines refer to amino acid position.

FIG. 4 illustrates the amino acid sequence of the K1 domain of plasminogen and the DNA sequence encoding it.

FIGS. 10 and 11 show the cDNA sequences and amino acid sequences of certain plasminogen activators.

FIG. 12, (A)–(I) illustrates the amino acid sequences of the finger domain of native t-PA and of consensus finger domains.

FIG. 15 shows the amino acid sequences of novel growth factor domains.

FIG. 16 illustrates the amino-terminal amino acid sequence of a representative hybrid fibrinolytic protein. Amino acids numbered 1–15 comprise the cross-linking domain. "t-PA" indicates the mature t-PA sequence shown in FIG. 1, beginning with amino acid number 1 (Ser).

BEST MODE FOR CARRYING OUT THE INVENTION

Figure 2:
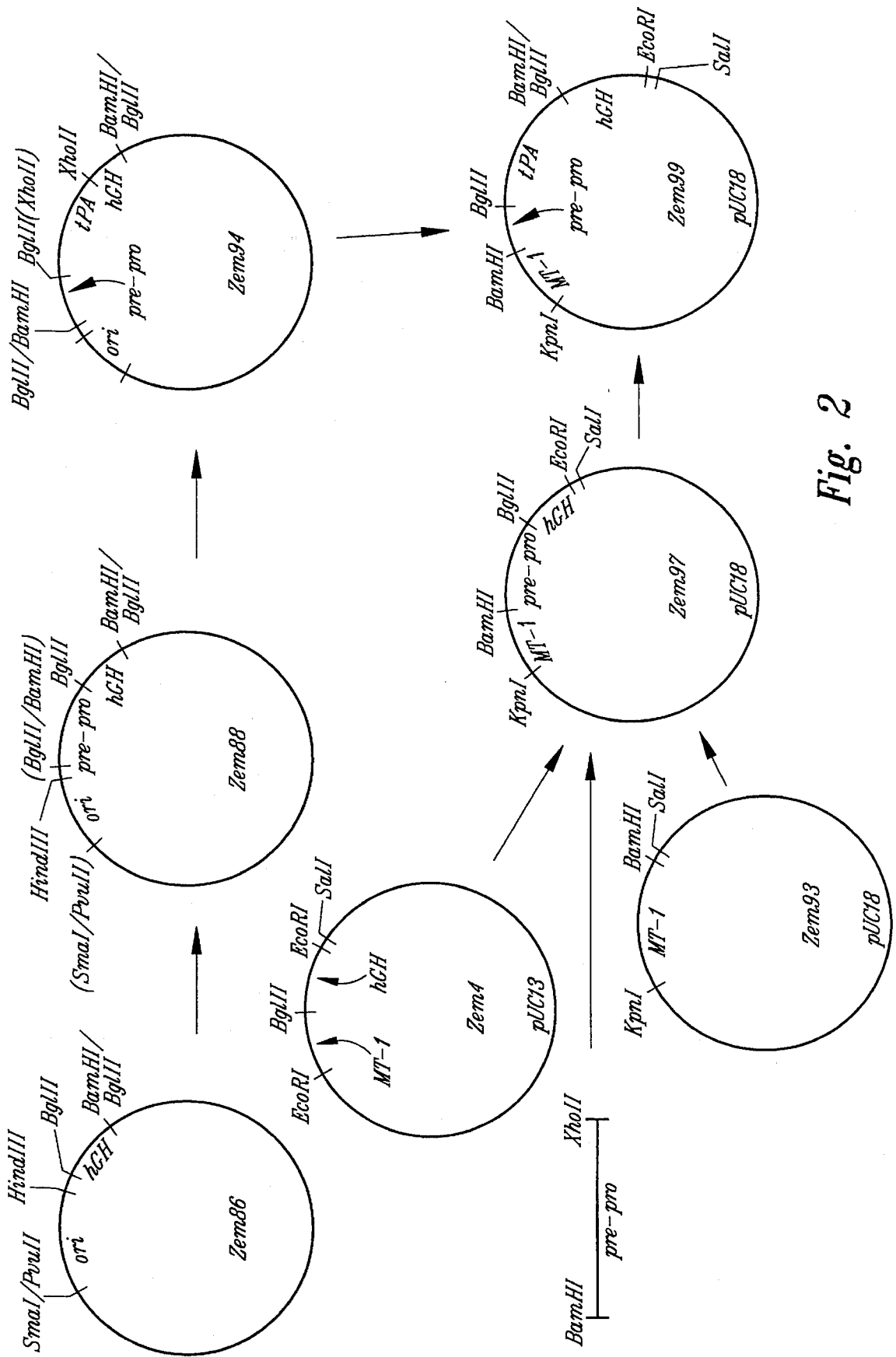
FIG. 2 illustrates the construction of the vector Zem99.

Prior to setting forth the invention, it may be helpful to an understanding thereof to define certain terms used herein.

DNA construct: A DNA molecule, or a clone of such a molecule, either single- or double-stranded, which has been constructed or modified through human intervention to contain segments of DNA combined and juxtaposed in a manner which would not otherwise exist in nature.

Plasmid or vector: A DNA construct containing genetic information which provides for its replication when inserted into a host cell. Replication may be autonomous or achieved by integration into the host cell genome. A plasmid generally contains at least one gene sequence to be expressed in the host cell, as well as sequences which encode functions that facilitate such gene expression, including promoters, transcription initiation sites and transcription terminators. The terms plasmid and vector include both linear and closed, circular molecules.

Domain: A three-dimensional, self-assembling array of amino acids of a protein molecule, which contains structural elements necessary for a specific biological activity of that protein.

Fibrin Binding Domain: That portion of a protein necessary for the binding of that protein to fibrin. For example, in native t-PA, the finger domain, growth factor domain and second kringle contribute individually and collectively to fibrin binding.

Plasminogen Activator: A protein which, in the presence of fibrin, can convert the pro-enzyme plasminogen into plasmin.

Native t-PA: A protein having the structure and biological activity of tissue plasminogen activator as isolated from human melanoma cells (see EP 41,766). Native t-PA has the amino acid sequence of the melanoma cell t-PA or may contain slight variations in sequence. Such variations, arising from, for example, genetic polymorphisms, will not substantially alter the structure of activity of the protein. Native t-PA may be isolated from cells which naturally produce it, or may be prepared from recombinant cells which have been transfected or transformed with a DNA sequence encoding native t-PA. The amino acid sequence of a representative native t-PA is shown in FIG. 1.

One of the elements of the coagulation cascade mentioned above is thrombin, an enzyme which catalyzes the conversion of fibrinogen to fibrin and activates zymogen factor XIII to factor XIIIa. Fibrin monomers polymerize, and the resulting polymers are covalently cross-linked via glutamine-lysine bridges by the transglutaminase factor XIIIa (reviewed by Lorand et al., *Prog. Hemostasis Thrombosis* 5: 245–290, 1980). Factor XIIIa can also catalyze other cross linking reactions, including cross linking $\alpha_2$-plasmin inhibitor (Sakata and Aoki, *J. Clin. Invest.* 65:290–297, 1980; Tamaki and Aoki, *Biochim. Biophys. Acta* 661:280–286, 1981), fibronectin (Mosher, *J. Biol. Chem.* 250: 6614–6621, 1975) and collagen (Mosher, et al. , *J. Clin Invest.* 64:781–787, 1979) to fibrin. The cross linking of $\alpha_2$-PI to fibrin is of physiological significance in that it regulates the resistance of the clot to lysis by plasmin (Aoki et al., *J. Clin Invest.* 63: 877–884, 1979). In this way a stable clot of high tensile strength is formed.

In accordance with the present invention, proteins and peptides having the capacity to bind covalently with a fibrin clot are combined with t-PA, urokinase or derivatives thereof to produce a novel class of highly clot-specific plasminogen activators. These activators comprise a cross-linking domain joined to a fibrin binding domain and a serine protease domain. The cross-linking domain combines with the fibrin binding domain to produce a molecule which binds strongly to fibrin and, once bound, forms a highly stable covalent complex.

Suitable cross-linking domains may be derived from proteins which act as acyl donor substrates in factor XIIIa-catalyzed cross-linking reactions. These proteins include $\alpha_2$-plasmin inhibitor, thrombospondin, βcasein, $\alpha_2$-macroglobulin, collagen, and factor V. The cross-linking domain contains at least one glutamine residue susceptible to factor XIIIa. The cross-linking function of $\alpha_2$-PI has been localized to the amino terminal 12 amino acids of this protein (Ichinose et al., *FEBS Lett* 153:369–371, 1983). In β-casein, glutamine-167 has been shown to be the susceptible residue, and 11 and 15 residue peptides derived from β-casein can act as factor XIIIa substrates (Gorman and Folk, *J. Biol. Chem.* 255:419–427, 1980). Similarly, the susceptible site in $\alpha_2$-macroglobulin has been localized to glutamine-670 (Sottrup-Jensen et al., *Ann. N.Y. Acad. Sci.* 421:41–60, 1983). The acyl donor activities of factor V (Francis et al., *J. Biol. Chem.* 261:9787–9792, 1986) and collagen and fibronectin (Mosher et al., *J. Biol. Chem.* 255:1181–1188, 1980) have also been analyzed. To identify a suitable cross-linking domain, an acyl donor protein is labeled with a lysine analog (e.g., dansylcadaverine or putrescene) and is then digested proteolytically, for example using trypsin, chymotrypsin, CNBr, etc. The resulting peptides are then separated and the labeled peptide is identified as containing the cross-linking domain. In general, it is preferred that the cross-linking domain of the proteins of the present invention be less than about 100 amino acids in length, preferably less than 40 amino acids in length and most preferably about 10 to 15 amino acids in length. A particularly preferred cross-linking domain is the amino acid sequence Asn-Gln-Glu-Gln-Val-Ser-Pro-Leu-Thr-Gly-Leu-Lys derived from the amino terminus of $\alpha_2$-PI.

The fibrin binding domain may be the complete heavy chain of t-PA or that of a t-PA analog. Suitable t-PA analogs have been described by, for example, Heyneker and Vehar (ibid.), Van Zonneveld et al. (*Proc. Natl. Acad. Sci. USA* 83:4670-4674, 1986); Robinson et al. (EP 207,589); Hung, et al. (published UK patent application 2,179,948), and Bang et al. (published Australian patent application 61804/86). These include analogs in which portions of the heavy chain have been deleted or replaced by other sequences. Particularly preferred are fibrin binding domains which are designed to maximize both binding to fibrin and stimulation of activity by fibrin. In this regard, preferred fibrin binding domains will include the K2 kringle of native t-PA in combination with a second kringle which binds fibrin with high affinity, including the K1, K4 and K5 kringles of plasminogen. Two copies of the K2 domain of native t-PA may also be used in tandem. The fibrin binding domain may contain the finger domain of native t-PA or another finger domain, the sequence of which is designed to enhance fibrin affinity. Specificity of the activator may also be enhanced by altering the sequence around the Arg(275)-Ile(276) activation site to make the molecule resistant to cleavage by plasmin. particularly preferred such alterations are the substitutions of Gly for Arg(275) and the substitution of Pro for Phe(274). The latter substitution results in a molecule which is is cleavable by thrombin.

The sequence may also be modified to increase the plasma half-life of the molecule. For example, it has been found that the growth factor domain is responsible, at least in part, for the rapid clearance of native t-PA from the plasma. By altering the sequence of a growth factor domain within the fibrin binding domain, the recognition site involved in this clearance may be removed. Particularly preferred sites for alteration are in the region of amino acids 48–90. Preferred alterations of the growth factor domain include amino acid substitutions based on the sequence of a growth factor domain From a protein with a long plasma half-life, such as coagulation factor IX. Other substitutions are made by designing consensus growth factor sequences based on sequences in factor VII, factor IX, protein C, epidermal growth factor, and other proteins containing growth factor-like regions. In general, these modifications will be designed so as to not drastically alter the overall chemical nature of the growth factor domain. In another preferred embodiment, a cysteine residue, particularly amino acid 84 (Cys), of the native t-PA growth factor domain is replaced by another amino acid, preferably Serine. If the fibrin binding domain includes the K1 kringle of native t-PA, it is preferred that the N-linked glycosylation site (Asn-X-Ser/Thr) be altered to block glycosylation, resulting in a reduced rate of clearance.

The serine protease domain may be derived from the light chain of t-PA or the heavy chain of urokinase. A cDNA encoding urokinase is disclosed by Heyneker et al. (EP 92,182). In one embodiment, the serine protease domain may be substantially the light chain of native t-PA or the heavy chain of urokinase. As used herein, the term "substantially" refers to an amino acid sequence corresponding to that of the native protein or having minor variations in the sequence which do not materially affect the biological properties of the protein. Alternatively, the native sequence may be modified so as to change certain of its properties. For example, amino acid substitutions may be made in the region near the activation site to alter the susceptibility of the protein to cleavage.

The hybrid proteins of the present invention may be prepared by combining genomic DNA sequences, cDNA sequences and/or synthesized oligonucleotides encoding the component polypeptides. A partial amino acid sequence of $\alpha_2$-PI is disclosed by Sumi et al. (*J. Biochem.* 100: 1399–1402, 1986). A cDNA sequence encoding native t-PA is disclosed by Pennica et al. (*Nature* 301: 214–221, 1983). DNA sequences encoding suitable analogs of t-PA are disclosed by, for example, Heyneker and Vehar (ibid.) Robinson (ibid.) and Hung et al. (ibid.), or may be constructed as described herein. Methods for synthesizing oligonucleotides are well known in the art, including the phosphotriester method of Crea et al. (*Proc. Natl. Acad. Sci. USA* 75: 5765, 1978). It is preferred to use an automated synthesizer, such as an Applied Biosystems Model 380A DNA synthesizer (Applied Biosystems, Inc., Foster City, Calif.). Additional alterations to the amino acid sequence are introduced through oligonucleotide-directed mutagenesis, generally as disclosed by Zoller and Smith (*Methods Enzymol* 100:468, 1983 and DNA 3: 479–488, 1984). Typically, a synthesized DNA fragment encoding a cross-linking domain is joined to sequences encoding the fibrin binding and serine protease domains. As described more fully in the examples which follow, suitable fibrin binding domain and serine protease domain sequences may be obtained from a cDNA encoding native t-PA. In certain preferred embodiments, the fibrin binding domain sequence of native t-PA is mutagenized to enhance binding and thereby increase the specificity of the resultant molecule. These coding sequences are then ligated to the sequence encoding a cross-linking domain. In certain instances, linker addition, blunt-end ligation or deletion mutagenesis may be used to obtain proper in-frame joining of sequences. Although it may be preferable to position the cross-linking domain at the amino terminus, this domain could be positioned elsewhere in the protein, so long as it does not interfere with other necessary functions, such as fibrin binding or serine protease activity.

Production of recombinant t-PA in bacteria, yeast, and mammalian cells is disclosed by, for example, Goeddel et al. (E/P 93,619 A1), Meyhack and Hinnen (EP 143,081 A2), and Gill (EP 174,835 A1). Methods for transfecting mammalian cells and for transforming bacteria and fungi with foreign DNA are well known in the art. Suitable expression vectors will comprise a promoter which is capable of directing the transcription of a foreign gene in a host cell and a functional transcription termination site. As will be recognized by those familiar with the art, it is, in some instances, preferred that expression vectors further comprise an origin of replication, as well as sequences which regulate and/or enhance expression levels, depending on the type of host cell selected. Suitable expression vectors may be derived from plasmids, RNA and DNA viruses or cellular DNA sequences, or may contain elements of each.

Preferred prokaryotic hosts for use in carrying out the present invention are strains of the bacteria *Escherichia coli*, although Bacillus and other genera are also useful. Techniques for transforming these hosts, and for expressing foreign DNA sequences cloned in them, are well known in the art (see, for example, Maniatis et al., eds ., *Molecular Cloning: A Laboratory Manual*, Cold Spring Harbor Laboratory, Cold Spring Harbor, N.Y., 1982). Vectors used for expressing foreign DNA in bacterial hosts will generally contain a selectable marker, such as a gene for antibiotic resistance, and a promoter which functions in the host cell. Appropriate promoters include the trp (Nichols and Yanofsky, *Meth. in Enzymology* 101:155, 1983), lac (Casadaban et al., *J. Bact.* 143:971–980, 1980), TAC (Russell et al., *Gene* 20:231–243, 1982), and phage λ promoter systems. Plasmids useful for transforming bacte ria include PBR322 (Bolivar et al., *Gene* 2:95–113, 1977) , the pUC plasmids (Messing, *Meth. in Enzymology* 101: 20–77 , 1983;. and Vieira and Messing, *Gene* 19:259–268, 1982) , pCQV2 (Queen, *J. Mol. Appl. Genet.* 2:1–10, 1983), and derivatives thereof.

Eukaryotic microorganisms, such as the yeast *Saccharomyces cerevisiae*, or filamentous fungi including Aspergillus species, may also be used as host cells. Particularly preferred species of Aspergillus include *A. nidulans* , *A. niger*, *A. oryzae*, and *A. terreus*. Techniques for transforming yeast are described, for example, by Beggs (*Nature* 275:104–108, 1978). Aspergillus species may be transformed according to known procedures, for example, that of Yelton et al. (*Proc. Natl. Acad. Sci. USA* 81:1740–1747, 1984). Expression vectors for use in yeast include YRp7 (Struhl et al., *Proc. Natl. Acad. Sci. USA* 76:1035–1039, 1979), YEp13 (Broach et al., *Gene* 8:121–133, 1979), pJDB248 and pJDB219 (Beggs, ibid.), and derivatives thereof. Such vectors will generally comprise a selectable marker, such as the nutritional marker TRP1, which allows selection in a host strain carrying a trp1 mutation, or the POT1 selectable marker, which permits selection in a tpi- strain grown in rich medium (Kawasaki and Bell, EP 171,142). Preferred promoters for use in yeast expression vectors include promoters from yeast glycolytic genes (Hitzeman et al., *J. Biol. Chem.* 255: 12073–12080, 1980; Alber and Kawasaki, *J. Mol. Appl. Genet.* 1:419–434, 1982; Kawasaki, U.S. Pat. No. 4,599, 311) or alcohol dehydrogenase genes (Young et al., in *Genetic Engineering of Microorganisms for Chemicals*, Hollaender et al., eds., p. 335, Plenum, N.Y., 1982; and Ammerer, *Meth. in Enzymology* 101:192–201, 1983). To facilitate purification of a modified t-PA protein produced in a yeast transformant and to obtain proper disulphide bond formation, a signal sequence from a yeast gene encoding a secreted protein may be substituted for the t-PA pre-pro sequence. A particularly preferred signal sequence is the pre-pro region of the MF α1 gene (Kurjan and Herskowitz, Cell 30:933–943, 1982; Kurjan et al., U.S. Pat. No. 4,546, 082 and Singh (EP 123,544)).

Higher eukaryotic cells may also serve as host cells in carrying out the present invention. Cultured mammalian cells, such as the BHK, CHO, NS-1, SP2/0, and J558L cell lines, are preferred. These and other cell lines are widely available, for example, from the American Type Culture Collection. A particularly preferred adherent cell line is the BHK cell line tk−ts[13] (Waechter and Baserga, *Proc. Natl. Acad. Sci USA* 79:1106–1110, 1982) hereinafter referred to as "tk⁻BHK cells." Expression vectors for use in mammalian cells comprise a promoter capable of directing the transcription of a cloned gene introduced into a mammalian cell. Particularly preferred promoters include the SV40 promoter (*Subramani et al., Mol. Cell Biol.* 1:854–864, 1981), the MT-1 promoter (Palmiter et al., *Science* 222:809–814, 1983), and the mouse kappa gene promoter (Bergman et al., *Proc. Natl. Acad. Sci. USA* 81:7041–7045, 1984). Also contained in the expression vectors is a transcription terminator, located downstream of the insertion site for the DNA sequence to be expressed. A preferred terminator is the human growth hormone (hGH) gene terminator (DeNoto et al., *Nuc. Acids Res.* 9:3719–3730, 1981). In addition, vectors will preferably contain enhancer sequences appropriate to the particular host cell line.

For expression of hybrid plasminogen activators in cultured mammalian cells, expression vectors containing cloned DNA sequences encoding the hybrid proteins are introduced into the cells by appropriate transfection techniques, such as calcium phosphate-mediated transfection (Graham and Van der Eb, *Virology* 52:456–467, 1973; as modified by Wiglet et al., *Proc. Natl. Acad. Sci. USA* 77:3567–3570, 1980; or as described by Loyter et al., *Proc. Natl. Acad. Sci. USA* 79:422, 1982) or electropotation (Neumann et al., *EMBO J.* 1:841–845, 1982). A small fraction of the cells integrate the DNA into their genomes or maintain the DNA in non-chromosomal nuclear structures. These transfectants can be identified by cotransfection with a gene that confers a selectable phenotype (a selectable marker). Selectable markers may be carried on the same vector as the sequence encoding the hybrid plasminogen activator, or may be carried on a separate vector, depending on the transfection protocol employed. Preferred selectable markers include the DHFR gene, which imparts cellular resistance to methotrexate (MTX), an inhibitor of nucleotide synthesis; or the bacterial neomycin resistance gene, which confers resistance to the drug G-418, an inhibitor of protein synthesis. After the host cells have taken up the DNA, drug selection is applied to select for a population of cells that are expressing the selectable marker at levels high enough to confer resistance.

The hybrid plasminogen activators of the present invention are preferably purified by affinity chromatography using polyclonal or monoclonal antibodies coupled to a suitable matrix, such as CNBr-activated Sepharose. Hybrid proteins containing fibrin binding and/or serine protease domains derived from native t-PA sequences may be purified using antibodies to native t-PA. Conventional chemical purification procedures, such as gel filtration, HPLC, etc. may also be employed.

The hybrid plasminogen activators of the present invention may be used within pharmaceutical compositions for the treatment of thrombosis, or as diagnostic compositions. The parmaceutical compositions will comprise the activators in combination with a carrier or diluent, such as sterile water or sterile saline, and may also comprise appropriate excipients and/or solvents. The resulting aqueous solutions may be packaged for use or filtered under aseptic conditions and lyophilized, the lyophilized preparation being combined with a sterile aqueous solution prior to administration.

Typically, an aqueous solution containing 3 g of mannitol and $10^6$ units of the activator is prepared under sterile conditions. One ml aliquots of this solution are pipetted into small vials, which are then lyophilized and sealed. For injection, the lyophilized material is combined with 2 ml of sterile water, the water being provided in a sealed ampoule. Administration is preferably by injection. The proteins of the present invention will typically be administered at doses of from about 6 mg to about 100 mg per patient, preferably between about 6 mg and 30 mg per patient, depending on the weight of the patient, the nature of the thrombus to be dissolved, and the specific activity of the activator. However, the present invention is not restricted to the above range and the dose may be varied depending on the condition. Determination of proper dose will be apparent to the skilled practitioner.

The hybrid plasminogen activators of the present invention may be labeled with a radioisotope or other imaging agent and used as diagnostic agents for imaging blood clots. Preferred radioisotope imaging agents include iodine-125 and technicium-99 with technicium-99 being particularly preferred. Methods for producing protein-isotope conjugates are well known in the art, and are described by, for example, Eckelman et al. (U.S. Pat. No. 4,652,440), Parker et al. (WO 87/05030) and Wilbur et al. (EP 203,764). Alternatively, the hybrid plasminogen activators may be bound to spin label enhancers and used for magnetic resonance (MR) imaging. Suitable spin label enhancers include stable, sterically hindered, free radical compounds such as nitroxides. Methods for labeling ligands for MR imaging are disclosed by, for example, Coffman et al. (U.S. Pat. No. 4,656,026). For administration, the labeled proteins are combined with a pharmaceutically acceptable carrier or diluent, such as sterile saline or sterile water. Administration is preferably by bolus injection, preferably intravenously. These imaging agents are particularly useful in identifying the location of clots in patients experiencing deep vein thrombosis, pulmonary embolism or other conditions in which the location of the thrombus is not obvious.

The following examples are given by way of illustration, and not by way of limitation.

EXAMPLES

Example 1

Construction of a Full-Length t-PA Clone

The sequence of a native human t-PA cDNA clone has been reported (Pennica et al., *Nature* 301: 214–221, 1983). The sequence encodes a pre-pro peptide of 32–35 amino acids followed by a 527–530 amino acid mature protein.

A cDNA clone comprising the coding sequence for mature t-PA was constructed using as starting material mRNA from the Bowes melanoma cell line (Rijken and Collen, *J. Biol. Chem.* 256: 7035–7041, 1981). This cDNA was then used to construct the plasmid pDR1296. *Escherichia coli* strain JM83 transformed with pDR1296 has been deposited with the American Type Culture Collection under Accession No. 53347.

Because the pre-pro sequence was not present in the cDNA clone pDR1296, it was constructed from synthesized oligonucleotides and subsequently joined to the cDNA. In the synthesized t-PA pre-pro sequence, cleavage sites for Bam HI and Nco I were introduced immediately 5' to the first codon (ATG) of the pre-pro sequence, and a Bgl II (Sau 3A, Xho II) site was maintained at the 3' end of the pre-pro sequence. The naturally-occurring pre-pro sequence lacks a convenient restriction site near the middle; however, the sequence GGAGCA (coding for amino acids −20 and −19, Gly-Ala) can be altered to GGCGCC to provide a Nat I site without changing the amino acid sequence.

To construct the pre-pro sequence, the following oligonucleotides were synthesized using an Applied Biosystems Model 380-A DNA synthesizer:

ZC131: 5' GGA TCC ATG GAT GCA ATG AAG AGA GGG CTC TGC TGT GTG³'

ZC132 5' TGG CGC CAC ACA GCA GCA GCA CAC AGC AGAG³'

ZC 133 5' GGC GCC GTC TTC GTT TCG CCC AGC CAG GAA ATC CATG³'

ZC134 5' AGA TCT GGC TCC TCT TCT GAA TCG GGC ATG GAT TTC CT³'

Following purification, oligomers ZC131 and ZC132 were annealed to produce an overlap of 12 base pairs (Section 1). Oligomers ZC133 and ZC134 were similarly annealed (Section 2). The oligomers were mixed in Pol I buffer (Bethesda Research Labs), heated to 65° C. for five minutes, and slowly cooled to room temperature for four hours to anneal. Ten units of DNA polymerase I were added and the reaction proceeded for two hours at room temperature. The mixtures were electrophoresed on an 8% polyacrylamide-urea sequencing gel at 1,000 volts for 2½ hours in order to size fractionate the reaction products. The correct size fragments (those in which the polymerase reaction went to completion) were cut from the gel and extracted.

After annealing, Section 1 was cut with Bam HI and Nar I and cloned into Bam HI+Nar I-cut pUC8 (Vieira and Messing, Gene 19: 259–268, 1982; and Messing, Meth. in Enzymology 101: 20–77, 1983). Section 2 was reannealed and cut with Nar I and Bgl II and cloned into Bam HI +Nar I-cut pUC8. Colonies were screened with the appropriate labeled oligonucleotides. Plasmids identified as positive by colony hybridization were sequenced to verify that the correct sequence had been cloned.

Section 1 was then purified from a Bam HI+Nar I double digest of the appropriate pUC clone. Section 2 was purified from a Nar I+Xho II digest. The two fragments were joined at the Nar I site and cloned into Bam HI-cut pUC8.

The t-PA sequence of pDR1296 was then joined to the synthesized pre-pro sequence in the following manner (FIG. 2). Plasmid pIC19R (Marsh et al., Gene 32: 481–486, 1984) was digested with Sma I and Hind III. The ori region of SV40 from map position 270 (Pvu II) to position 5171 (Hind III) was then ligated to the linearized pIC19R to produce plasmid Zem67. This plasmid was then cleaved with Bgl II and the terminator region from the human growth hormone gene (De Noto et al., Nuc. Acids Res. 9: 3719–3730, 1981) was inserted as a Bgl II-Bam HI fragment to produce plasmid Zem86. The synthesized t-PA pre-pro sequence was removed from the pUC8 vector by digestion with Bam HI and Xho II. This fragment was inserted into Bgl II-digested Zem86 to produce plasmid Zem88. Plasmid pDR1296 was digested with Bgl II and Bam HI and the t-PA cDNA fragment was isolated and inserted into Bgl II-cut Zem88. The resultant plasmid was designated Zem94.

The vector Zem99, comprising the MT-1 promoter, complete t-PA coding sequence, and the hGH terminator, was then assembled in the following manner (FIG. 2). A Kpn I-Bam HI fragment comprising the MT-1 promoter was isolated from MThGH111 (Palmiter et al., Science 222: 809–814, 1983) and inserted into pUC18 to construct Zem93. Plasmid MThGH112 (Palmiter et al., ibid.) was digested with Bgl II and religated to eliminate the hGH coding sequence. The MT-1 promoter and hGH terminator were then isolated as an Eco RI fragment and inserted into pUC13 to construct Zem4. Zem93 was then linearized by digestion with Bam HI and Sal I. Zem4 was digested with Bgl II and Sal I and the hGH terminator was purified. The t-PA pre-pro sequence was removed from the pUC8 vector as a Bam HI-Xho II fragment. The three DNA fragments were then joined and a plasmid having the structure of Zem97 (FIG. 2) was selected. Zem97 was cut with Bgl II and the Xho II t-PA fragment from Zem94 was inserted. The resultant vector is Zem99.

Example 2

Construction of Vector Zem219

Figure 3:
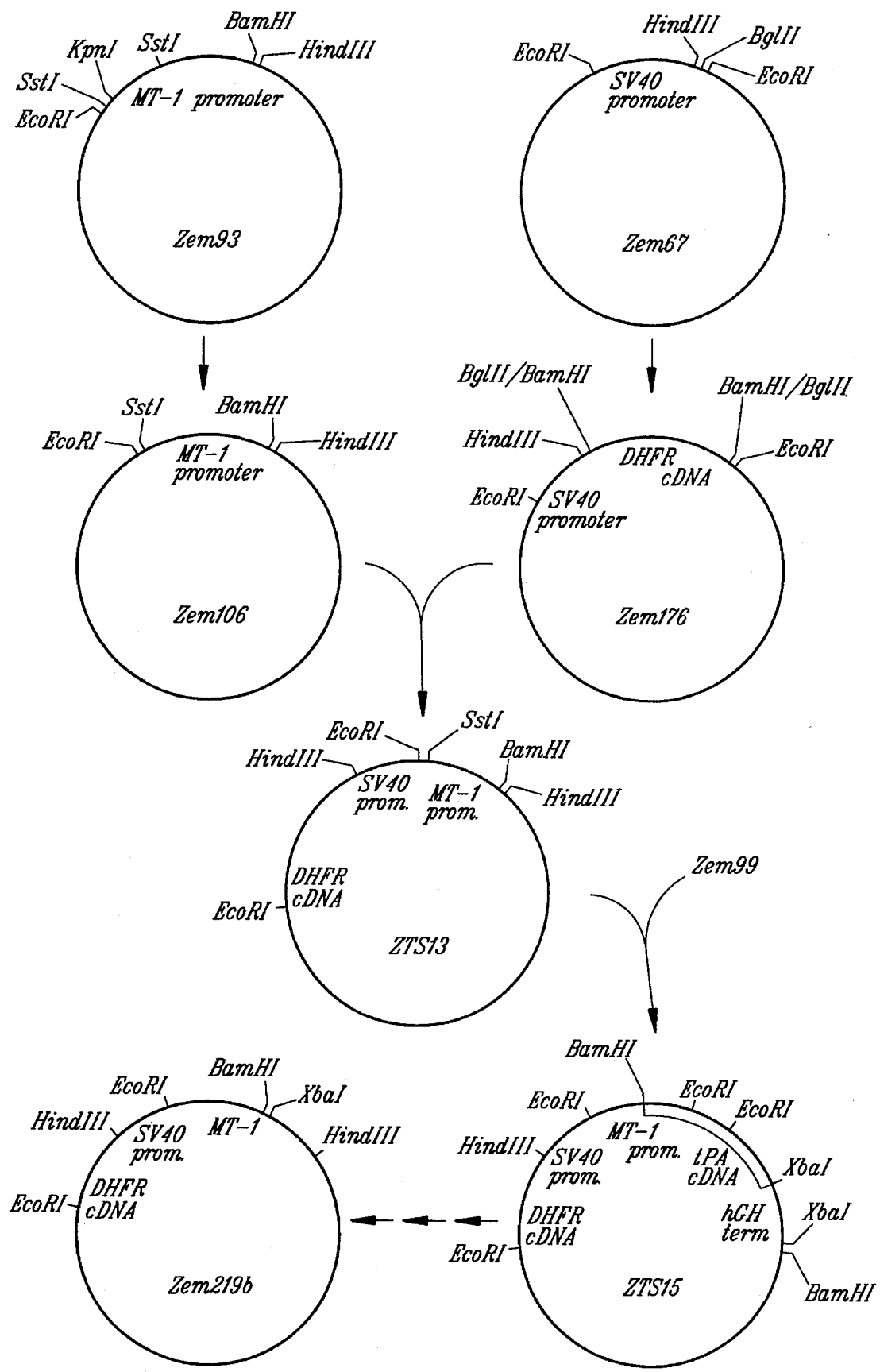
FIG. 3 illustrates the construction of vector Zem219b.

Plasmid pSV2-DHFR (Subramani et al., ibid.) was digested with Cfo I, and the fragment containing the DHFR cDNA and the 3' attached SV40 sequences was isolated, repaired, and ligated to Bam HI linkers. After digestion with Bam HI, an approximately 800 bp fragment containing the entire cDNA and the SV40 terminator region was purified and ligated to Bam HI-digested pUC8. Zem67 (Example 1) was digested with Bgl II and ligated with the Bam HI DHFR-SV40 fragment to generate plasmid Zem176. Plasmid Zem93 was digested with Sst I and re-ligated to generate plasmid Zem106, in which approximately 600 bp of sequence 5' to the MT-1 promoter were eliminated. Plasmid Zem106 was digested with Eco RI and ligated to the Eco RI fragment containing the DHFR gene from plasmid Zem176. The resulting plasmid was designated Zts13. Plasmid Zts13 was digested with Bam HI and ligated to the Bam HI fragment from plasmid Zem99 containing the entire t-PA coding region and hGH terminator sequence. The resulting plasmid was designated Zts15. Zts15 was partially digested with Bam HI, repaired, re-ligated and transformed to generate plasmid Zem219, in which the 3' Bam HI site was destroyed. Plasmid Zem219 was partially digested with Xba I, repaired, re-ligated and transformed to generate plasmid Zem219a, in which the 3' Xba I site was destroyed. Plasmid Zem219 a was digested with Bam HI and Xba I, the vector sequences purified away from the t-PA cDNA sequences, and ligated with an oligomeric Bam HI-Xba I adaptor to generate the expression vector Zem219 (FIG. 3), into which mutagenized Bam HI-Xba I t-PA sequences were subsequently inserted.

Example 3

Construction of DNA Sequences Encoding the K1 Domain of Plasminogen

Plasmid pK1 comprises a coding sequence for the K1 domain of plasminogen, the sequence of which is shown in FIG. 4. It was constructed from a series of eleven oligonucleotides designated PK1-1, PK1-2, PK1-3–PK1-12, the sequences of which are shown in Table 1.

TABLE 1

| Oligonucleotide | Sequence |
| --- | --- |
| PK1-1 | 5'GAT CCA CGC GTG CCA CGT GCA AGA CCG GTG ATG GTA AAA ACT ACC GAG GTA CCA TGT CCA AGA CC3' |
| PK1-2 | 5'AAA AAC GGT ATT ACA TGT CAG AAA TGG TCA TCT |

TABLE 1-continued

| Oligonucleotide | Sequence |
| --- | --- |
| | ACT AGT CCA CAC CGG CCG CGG TTT TCT³' |
| PK1-3 | 5'CCA GCT ACC CAT CCA TCT GAA GGC CTG GAA GAG AAT TAC TGT AGG AAT CCA GAT AAC GAT³' |
| PK1-4 | 5'CCT CAG GGT CCC TGG TGT TAC ACC ACA GAC CCC GAG AAG AGG TAC GAC TAC TGC GAT ATC GCA TG³' |
| PK1-5 | 5'CCG TTT TTG GTC TTG G³' |
| PK1-6 | 5'GTA GCT GGA GAA AAC CG³' |
| PK1-7 | 5'CCC TGA GGA TCG TTA TC³' |
| PK1-9 | 5'CGA TAT CGC AGT AGT CGT ACC TCT TCT C³' |
| PK1-10 | 5'GAT CCT CAG GGT CCC TGG TGT TAC ACC ACA³' |
| PK1-11 | 5'GAC CCC GAG AAG AGG TAC GAC TAC TGC GAT ATC GCA TG³' |
| PK1-12 | 5'GGG GTC TGT GGT GTA ACA CCA GGG ACC CTG AG³' |

The coding sequence for nucleotides 1 through 182 of the plasminogen K1 domain was constructed from oligonucleotides PK1-1 through PK1-7 in the following manner. 100 pmole each of the oligonucleotides PK1-1, PK1-2, PK1-3 and PK1-4 were phosphorylated at their 5' termini. The phosphorylated oligonucleotides were mixed with 100 pmole each of PK1-5, PK1-6, and PK1-7. The mixture was precipitated with ethanol and the precipitate was resuspended in H₂O and heated for three minutes at 90° C. The solution was then left to stand at room temperature for ten minutes, then placed on ice. To the chilled mixture was added 10 μl of 660 mM Tris HCl, pH 7.6, containing 6.6 mM MgCl₂, 10 μl of 0.1M dithiothreitol, 10 μl of 5 mM ATP, and 1000 units of T₄ DNA ligase. The mixture was incubated 15 hours at 14° C. Ethanol was added and the precipitate was resuspended in 20 μl of TE buffer (10 mM Tris HCl, 1 mm EDTA, pH 8.0), followed by the addition of an equal volume of alkali loading buffer (20 mM NaCl, 2 mM EDTA, 80% formamide, 0.1% xylene cyanol and 0.1% bromphenol blue). The mixture was heated for three minutes at 90° C. and electrophoresed on a 6% polyacrylamide gel containing 8.4M urea for one hour at 300 volts. The gel was stained with ethidium bromide, and a 250 bp band was recovered by electrophoretic transfer to DEAE-cellulose paper (Dretzen et al., *Anal. Biochem.* 112: 295–298, 1981). The recovered DNA was solubilized in 100 μl of TE buffer and the fragment was designated PK1-n. PK1-n was C-tailed at the 3' terminus by combining 10 μl of the PK1-n solution with 2 μl of 100 mM sodium cacodylate—25 mM HEPES, pH 7.6, 6.2 μl of 1 mM dCTP, 10 units terminal deoxynucleotidyl transferase and 5 μl of H₂O. The reaction mix was incubated at 37° C. for ten minutes, then extracted with phenol:chloroform (1:1).

One μl of 3'-oligo (dG) tailed pUC9 (obtained from Pharmacia) was cleaved with Sma I. The linearized, tailed plasmid was added to the C-tailed PK1-n. The mixture was then ethanol-precipitated, and the DNA was resuspended in 0.5 μl of 2M KCl and 9.5 μl of TE buffer, and incubated at 65° C. for 10 minutes, then cooled to room temperature. To the cooled mixture were added 5 μl of 0.2M Tris HCl, pH 7.5, containing 0.1M MgCl₂ and 0.1M dithiothreitol, 20 μl of 2.5 mM dNTPs, 10 μl of 5 mM ATP, 53 μl H₂O, 5 units DNA polymerase I (Klenow fragment), and 300 units T₄ DNA ligase (final volume of 100 μl). The mixture was incubated at 14° C. for 12 hours, then used to transfect *E. coli* JM83.

The transfected JM83 cells were probed with PK1-6 using the method of Wallace et al. (*Nuc. Acids Res.* 9: 879–894, 1981). Twenty positive clones were sequenced and two were selected, #1–3, including base pairs 1–170, and #8–5, including base pairs 68–186 (see FIG. 5).

Figures 5, 6:
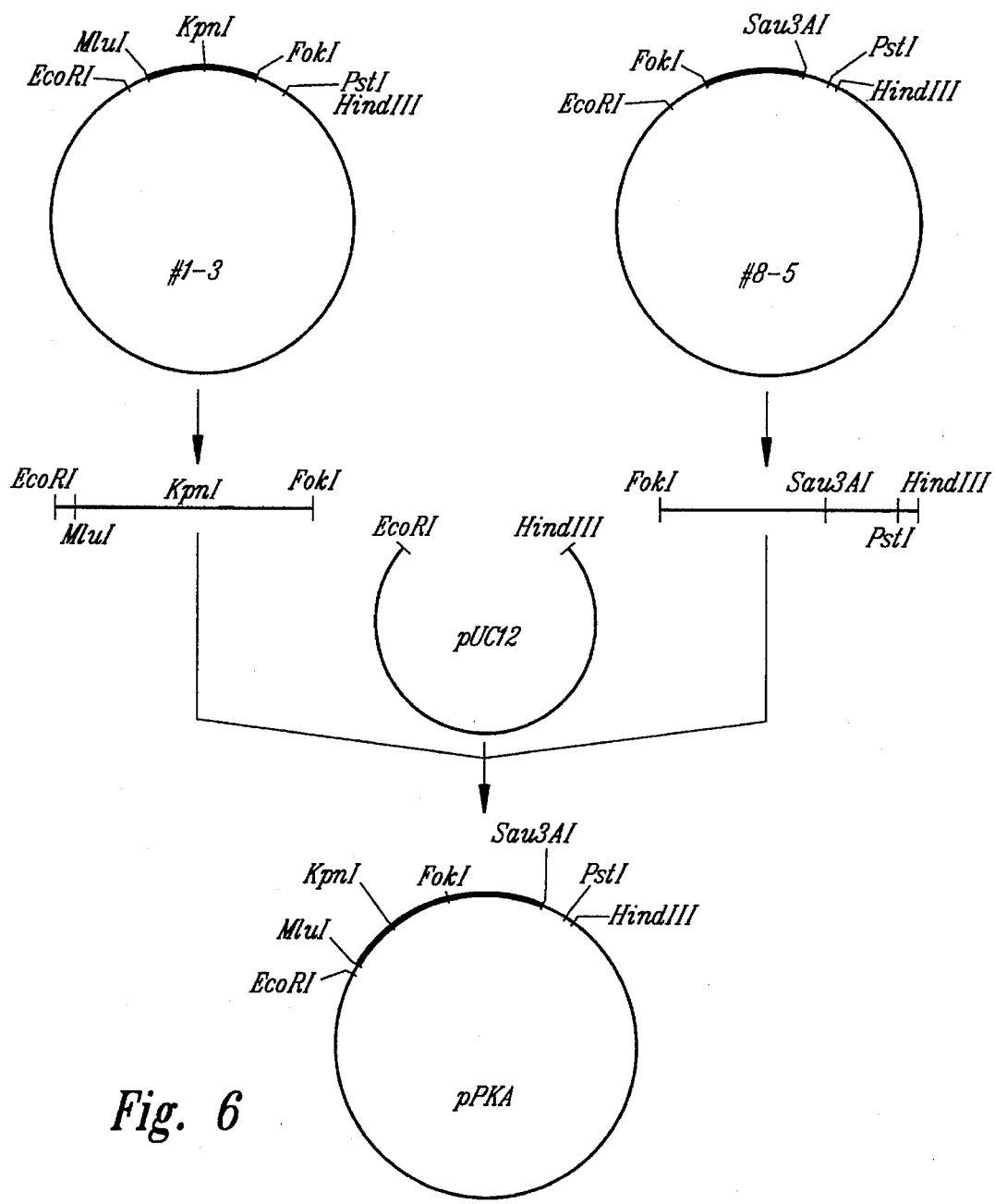
FIG. 5 shows partial restriction maps of clones #1–3 and #8–5, which encode portions of the plasminogen K1 domain.
FIG. 6 illustrates the construction of plasmid pPKA.

Referring to FIG. 6, clone #1–3 was digested with Eco RI and Fok I, and a 130 bp fragment containing a Kpn I site was recovered. Similarly, clone #8–5 was digested with Fok I and Hind III, and a 90 bp fragment was recovered. The two fragments were joined to Eco RI, Hind III-digested pUC12, and the resultant plasmid was designated pPKA. This plasmid thus contains a DNA sequence corresponding to nucleotides 1–182 of the plasminogen K1 sequence.

The remainder of the K1 sequence was constructed using oligonucleotides PK1-9, PK1-10, PK1-11 and PK1-12. One pmole each of the oligonucleotides was phosphorylated at the 5' end and the combined oligos were mixed with 40 ng of Bam HI, Sph I-digested M13tg130 RF (obtained from Amersham). To this mixture were added 4 μl of 660 mM Tris HCl, pH 7.6 containing 66 mM MgCl₂, and 22 μl of H₂O. The solution was heated for three minutes at 90° C. and allowed to cool to room temperature over a period of one hour. Four μl of 0.1M dithiothreitol, 4 μl of 5 mM ATP, and 300 units of T₄ DNA ligase were added, and the mixture was incubated for 12 hours at 14° C. The resulting phage clone, designated M13PKB RF (FIG. 7), contained nucleotides 183 through 250 of the K1 sequence.

Figure 7:
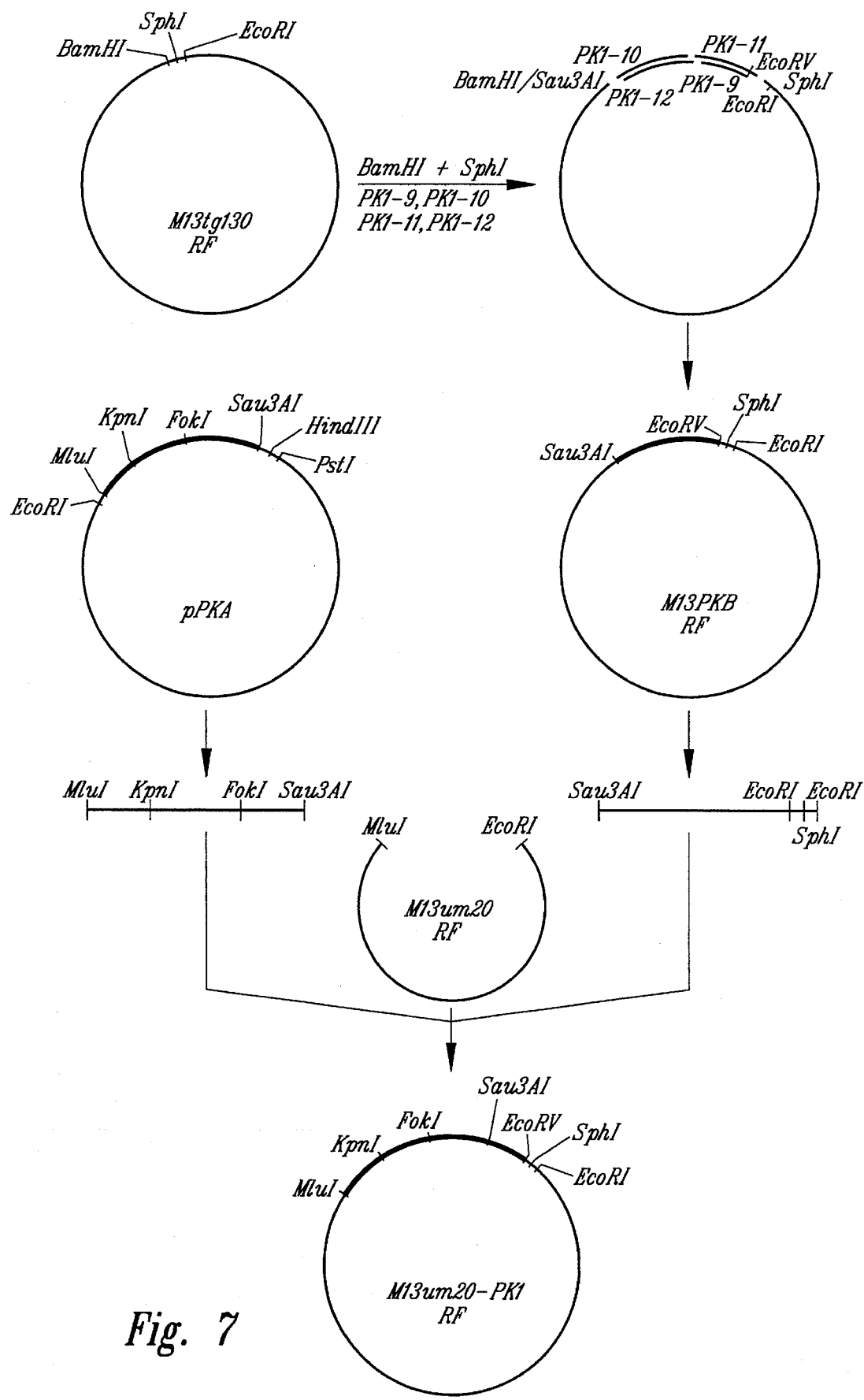
FIG. 7 illustrates the construction of a vector containing the plasinogen K1 coding sequence.

The assembly of the complete K1 coding sequence is illustrated in FIG. 7. Plasmid pPKA was digested with Mlu I and Sau 3AI, and a 176 bp fragment was recovered. M13PKB RF was digested with Sau 3AI and Eco RI, and an 88 bp fragment was recovered. These fragments were joined to Mlu I, Eco RI-digested M13um20 RF (obtained from IBI), and the resultant plasmid was designated M13um20-PK1.

Figure 8:
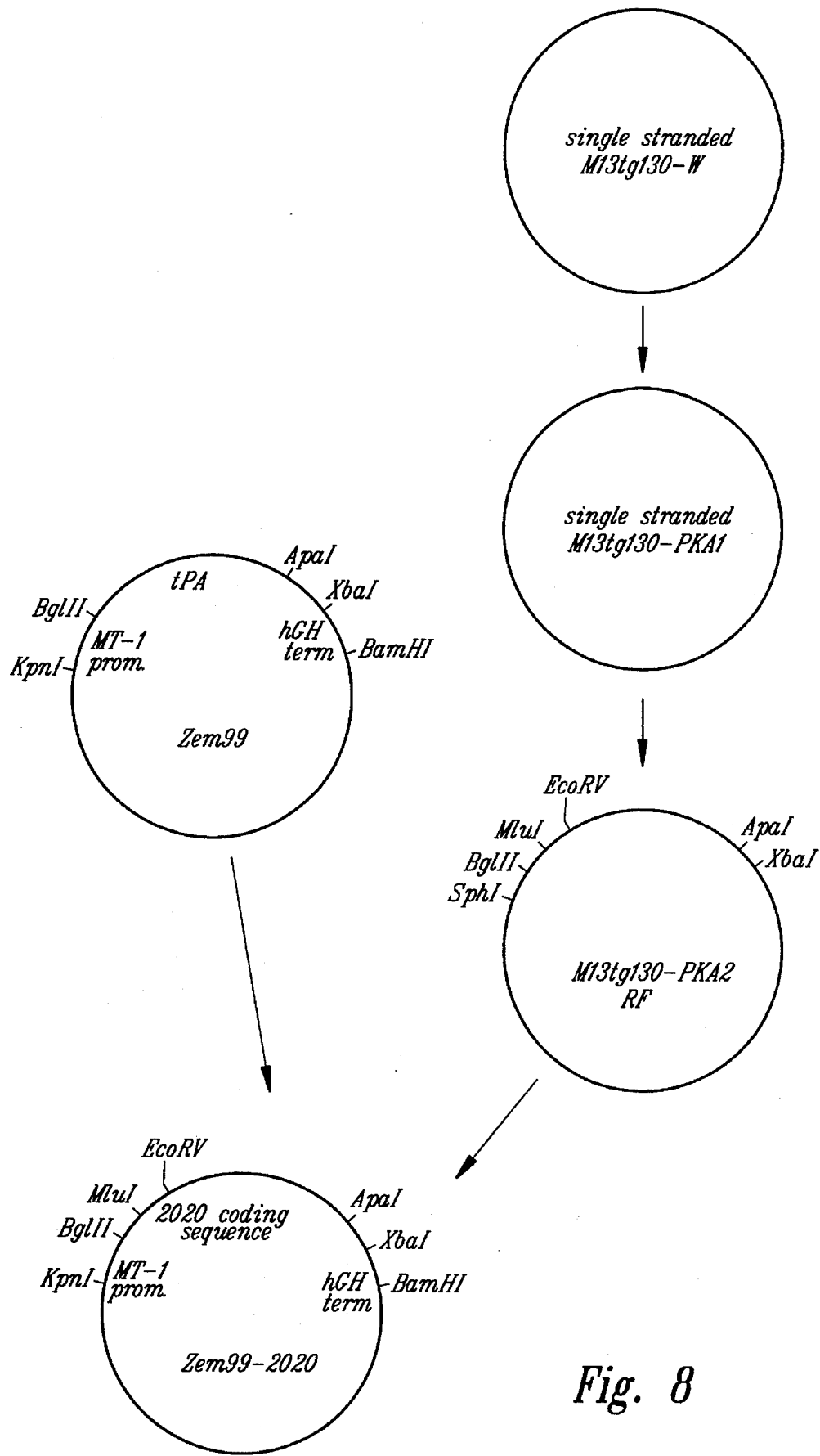
FIG. 8 illustrates the construction of plasmid Zem99-2020.
Figure 9:
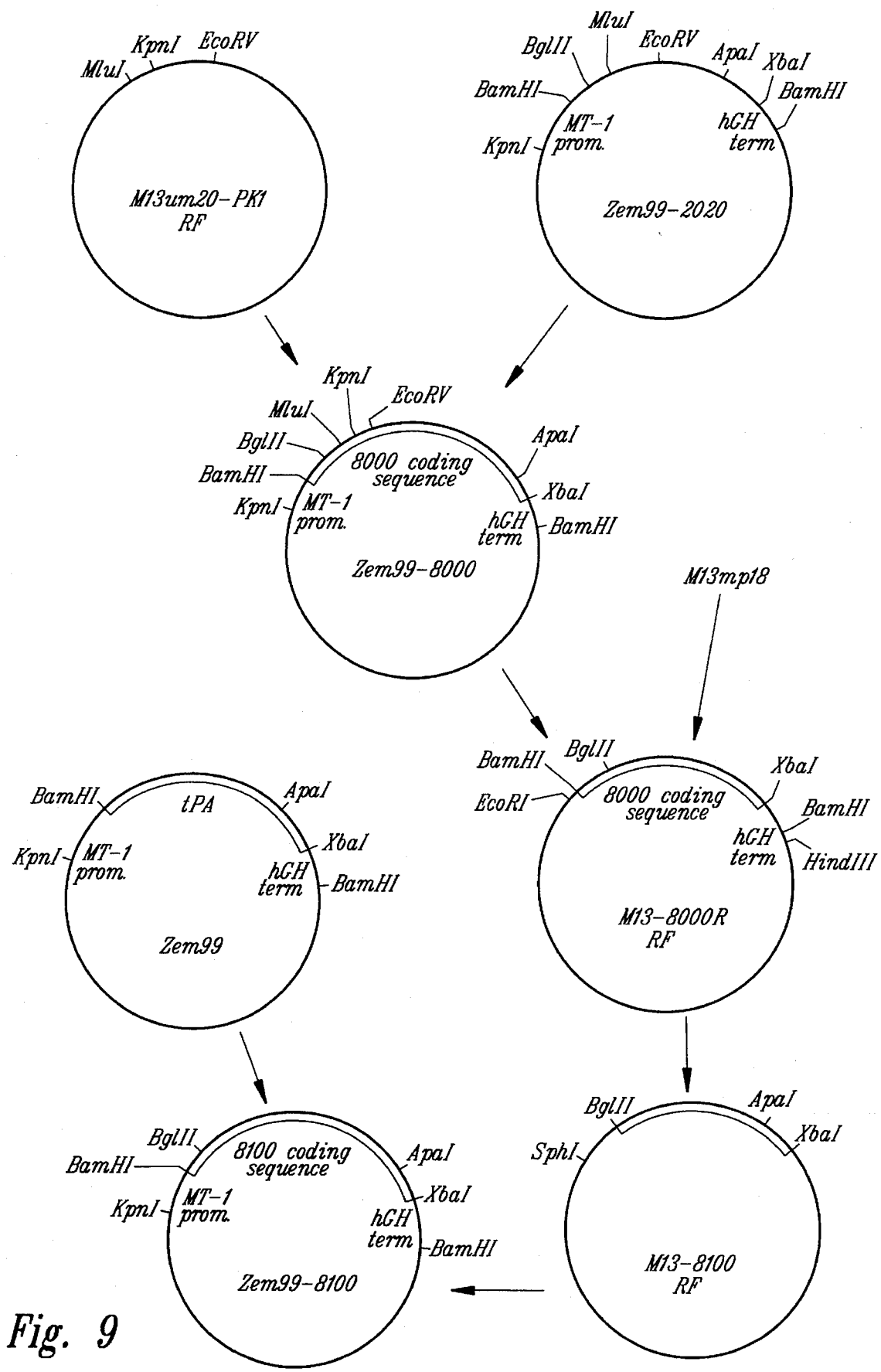
FIG. 9 illustrates the construction of the plasmids Zem99-8000 and Zem99-8100.

The PK1 coding sequence was then inserted into the t-PA cDNA as a replacement for the t-PA kringle 1 sequence (FIGS. 8 and 9). The t-PA sequence was first mutagenized to insert Mlu I and Eco RV sites. Plasmid pDR1496 was digested with Sph I and Xba I, and the 2.1 kb fragment comprising the alpha factor and t-PA sequences was isolated. (*S. cerevisiae* strain ES-11c transformed with pDR1496 has been deposited with American Type Culture Collection under Accession Number 20728.) This fragment was joined to Sph I, Xba I-digested M13tg130 replicative form (RF), and the resultant phage was designated M13tg130-W. Single-stranded phage DNA was then annealed to an oligonucleotide (5'GCA CGT GGC ACG CGT ATC TAT TTC³'), and mutagenesis was carried out according to standard procedures. The mutagenized phage was designated M13tg130-PKA1. Single-stranded DNA of M13tg130-PKA1 was isolated and mutagenized with an oligonucleotide having the sequence 5'CTC AGA GCA TTC CAG GAT ATC GCA GAA CTC³'. Single-stranded DNA was prepared from the mutagenized phage and sequenced. A clone containing an Mlu I site at the 5' end and an Eco RV site at the 3' end of the Kringle 1 coding sequence was selected and designated M13tg130-PKA2 (FIG. 8).

Replicative form DNA was prepared from M13tg130-PKA2 and was digested with Bgl II and Apa I. The fragment containing the Mlu I and Eco RV sites was recovered and joined to Bgl II, Apa I-digested Zem99, as shown in FIG. 8. The resultant plasmid was designated Zem99-2020.

The PK1 sequence was then inserted into the t-PA cDNA. M13um20-PK1RF was digested with Mlu I and Eco RV, and the 336 bp fragment was recovered. This fragment was joined to Mlu I, Eco RV-digested Zem99-2020 to construct Zem99-8000 (FIG. 9). The mutant t-PA coding sequence of Zem99-8000 and the encoded amino acid sequence are shown in FIG. 10. *E. coli* RRI transformed with Zem99-8000 has been deposited with the Fermentation Research Institute (FRI), Agency of Industrial Science and Technology, Ministry of International Trade and Industry, Japan, under Accession No. FERM P-9272.

A second plasminogen K1 sequence encoding Ash at position 96 was also constructed (FIG. 9). Zem99-8000 was digested with Bam HI, and the fragment containing the Bgl II site was recovered. This fragment was joined to Bam HI-cut M13mp18 to construct M13-8000R. An oligonucleotide primer (sequence $^5$'TTT TTA CCA TTA CCG GTC TT$^3$') was annealed to single-stranded M13-8000R, and mutagenesis was carried out according to routine procedures. Clones were screened and sequenced, and double-stranded DNA, designated M13-8000RF, was prepared from a positive clone. This phage was digested with Bgl II and Apa I, and the t-PA fragment was isolated and joined to Bgl II, Apa I-cut Zem99. The resultant plasmid was designated Zem99-8100. The t-PA coding sequence present in Zem99-8100 and the encoded amino acid sequence are shown in FIG. 11. *E. coli* RR1 transformed with Zem99-8100 has been deposited with the Fermentation Research Institute under Accession No. FERM P-9315.

Example 4

Replacement of the Finger Domain with Consensus Finger Sequences

Replacement of the t-PA finger domain with a consensus finger region results in the elimination of potential proteolytic cleavage sites at Arg-27 and Lys-49. Eight finger replacement sequences were constructed, based on an analysis of the finger domains of fibronectin and t-PA. The amino acid sequences of these "consensus" finger domains are shown in FIG. 12 and Table 2.

The consensus finger sequences were constructed from oligonucleotides as described in Section B, below, then inserted into the t-PA coding sequence. To facilitate this insertion, a Kpn I site was introduced downstream (3') of the region encoding the wild-type finger domain. Digestion of the resulting sequence with Bgl II and Kpn I resulted in the deletion of the native finger domain.

A. Kpn I Site Insertion Between the Finger and Growth Factor Domains

In order to place a Kpn I site after the native finger domain coding sequence in the t-PA cDNA, a mutagenesis was performed with oligonucleotide ZC986 (5'TTT GAC AGG TAC CGA GTG GCA$^3$'). DNA of a phage M13 clone containing the 5' Bam HI-Eco RI fragment of the t-PA cDNA was prepared. 100 µl of this solution was used to infect *E. coli* RZ1032 in 100 µl of YT medium supplemented with 0.1 µg/ml uridine. This culture was incubated at 37° C., with vigorous shaking, overnight. Growing the M13 in strain RZ1032 produces phage containing uridine which are viable in strain RZ1032 but not in *E. coli* strain JM101.

The cells were spun out, and the phage supernatant was used to reinfect *E. coli* RZ1032. This second passage was performed to dilute out any JM101-derived phage which contained no uracil. Again, the cells were spun out and the phage were plated on strains JM101 and RZ1032. Normal viability was observed on RZ1032 plates (indicating phage at $10^9$ pfu/ml), but no plaques were observed on JM101 cells. A complementary strand primed with the mutagenic oligonucleotide was then produced in vitro. The new strand, containing the mutation, contained thymidine and was therefore viable in strain JM101; the wild-type template was not.

Template DNA was prepared by PEG precipitation of the phage supernatant followed by phenol-chloroform extraction and ethanol precipitation. One µg of this template DNA was hybridized with 10 µg of oligonucleotide ZC986 by briefly boiling, incubating at 65° C. for 5 minutes, and then slowly bringing the temperature down to 4° C. before adding 10 µl 0.2M HEPES pH 7.8, 2 µl 100 mM DTT, 1 µl 1M MgCl$_2$, 20 µl 2.5 mM each dNTP, 10 µl 10 mM ATP, 1 1 2.5 U/µl DNA polymerase I (Klenow fragment) and 2 µl 1U/µl T$_4$ DNA ligase, final volume adjusted to 100 µl with H$_2$O. After extension at 37° C. for 2 hours, the DNA was transfected into competent JM101 cells. A control extension (minus oligonucleotide) was performed to compare the amount of background produced by extension by priming on contaminating RNA or DNA species. The transfection produced zero plaques with unmutagenized template, 150 on control extension (minus oligonucleotide) and 300 with mutagenized template.

The plates were screened by hybridizing a plaque lift with $^{32}$p-labeled mutagenic oligonucleotide and washing in 3M TMACl (Wood et al., *Proc. Natl. Acad. Sci. USA* 82: 1585-1588, 1985) at Tm-5° C. for 30 minutes and also by sequencing randomly picked plaques. One positive clone was obtained.

B. Production of Finger Replacement Domains

DNA sequences encoding the finger region replacements shown in Table 2 and FIG. 12 were constructed.

TABLE 2

| Finger | Encoded Amino Acid Sequence | Oligonucleotides* |
| --- | --- | --- |
| t-PA wild-type: | CRDEKTQMIYQQHQSWLRPVLR-SNRVEYCWC--N-SGRAQC | |
| Consensus 1: | CFD--NGKSYKIGETWERPYE--GFMLS-CTCLGNGRGEFRC | (ABC) |
| Consensus 2: | CHDEKTGSSYKIGEQWERPYL-SGNRLE-CTCLGNGSGRWQC | (DEF) |
| Consensus 3: | CFD--NGKSYKIGETWERPYE--GFMLS-CTCLGNGSGRWQC | (ABF) |
| Consensus 4: | CFD--NGKSYKIGEQWERPYL-SGNRLE-CTCLGNGRGEFRC | (AEC) |
| Consensus 5: | CFD--NGKSYKIGEQWERPYL-SGNRLE-CTCLGNGSGRWQC | (AEF) |
| Consensus 6: | CHDEKTGSSYKIGETWERPYE--GFMLS-CTCLGNGSGRWQC | (DBF) |
| Consensus 7: | CHDEKTGSSYKIGEQWERPYL-SGNRLE-CTCLGNGRGEFRC | (DEC) |
| Consensus 8: | CHDEKTGSSYKIGETWERPYE--GFMLS-CTCLGNGRGEFRC | (DBC) |

*A = ZC1116/1117

TABLE 2-continued

| Finger | Encoded Amino Acid Sequence | Oligonucleotides* |
|---|---|---|

B = ZC1118/1119
C = ZC1120/1121
D = ZC1122/1123
E = ZC1124/1125
F = ZC1126/1127

TABLE 3

| ZC1116 | | | | | | | | | | | | | | |
|---|---|---|---|---|---|---|---|---|---|---|---|---|---|---|
| GAT | CTT | ATC | AAG | TCA | TAT | GTT | TTG | ATA | ATG | GAA | AAT | CTT | ATA | A |
| ZC1117 | | | | | | | | | | | | | | |
| CTC | CAA | TTT | TAT | AAG | ATT | TTC | CAT | TAT | CAA | AAC | ATA | TGA | CTT | GAT |
| AA | | | | | | | | | | | | | | |
| ZC1118 | | | | | | | | | | | | | | |
| AAT | TGG | AGA | AAC | ATG | GGA | ACG | GCC | GTA | TGA | AGG | ATT | TAT | GCT | TTC |
| T | | | | | | | | | | | | | | |
| ZC1119 | | | | | | | | | | | | | | |
| CAT | GTA | CAA | GAA | AGC | ATA | AAT | CCT | TCA | TAC | GGC | CGT | TCC | CAT | GTT |
| T | | | | | | | | | | | | | | |
| ZC1120 | | | | | | | | | | | | | | |
| TGT | ACA | TGC | CTA | GGA | AAT | GGC | CGC | GGA | GAA | TTT | AGA | TGT | CAT | TCG |
| GTA | C | | | | | | | | | | | | | |
| ZC1121 | | | | | | | | | | | | | | |
| CGA | ATG | ACA | TCT | AAA | TTC | TCC | GCG | GCC | ATT | TCC | TAG | G | | |
| ZC1122 | | | | | | | | | | | | | | |
| GAT | CTT | ATC | AAG | TCA | TAT | GTC | ATG | ATG | AAA | AAA | CAG | GCT | CGA | GTT |
| ATA | A | | | | | | | | | | | | | |
| ZC1123 | | | | | | | | | | | | | | |
| CTC | CAA | TTT | TAT | AAC | TCG | AGC | CTG | TTT | TTT | CAT | CAT | GAC | ATA | TGA |
| CTT | GAT | AA | | | | | | | | | | | | |
| ZC1124 | | | | | | | | | | | | | | |
| AAT | TGG | AGA | ACA | ATG | GGA | ACG | GCC | GTA | TCT | TTC | TGG | AAA | TCG | ATT |
| AGA | A | | | | | | | | | | | | | |
| ZC1125 | | | | | | | | | | | | | | |
| CAT | GTA | CAT | TCT | AAT | CGA | TTT | CCA | GAA | AGA | TAC | GGC | CGT | TCC | CAT |
| TGT | T | | | | | | | | | | | | | |
| ZC1126 | | | | | | | | | | | | | | |
| TGT | ACA | TGC | CTA | GGA | AAT | GGT | TCC | GGA | AGA | TGG | CAA | TGT | CAT | TCG |
| GTA | C | | | | | | | | | | | | | |
| Z1127 | | | | | | | | | | | | | | |
| CGA | ATG | ACA | TTG | CCA | TCT | TCC | GGA | ACC | ATT | TCC | TAG | G | | |

The eight consensus sequences were generated from the indicated oligonucleotides (Table 3). The oligonucleotides were produced using an Applied Biosystems Model 380A DNA synthesizer. First, the twelve oligonucleotides were kinased and simultaneously labeled to a low specific activity with $\gamma$-$^{32}$p ATP by incubating each with polynucleotide kinase at 37° C. for ½ hour. Then the indicated eight combinations (ABC, DEF, ABF, AEC, AEF, DBF, DEC and DBC) were produced by mixing the appropriate oligonucleotides, adding DNA ligase, and incubating at 37° C. for 1 hour. The products of this reaction were sorted out on a 6% polyacrylamide-8M urea sequencing gel. The bands corresponding to the DNA coding for full-length finger domains were cut out, and the DNA was eluted in 2.5M ammonium acetate. The DNA was ethanol-precipitated and resuspended in water to a concentration of 1 pmole/µl.

Replicative form (RF) DNA was prepared from the positive clone described in Example 4A, and the Bam HI to Eco RI t-PA fragment was purified. Plasmid Zem219a (described in Example 2) was digested with Xba I and then partially digested with Eco RI. The 1010 bp fragment, containing the 3' t-PA coding region, was purified. plasmid Zem219b (described in Example 2) was digested with Bam HI and Xba I and ligated to the 5' t-PA fragment (Bam HI-Eco RI) and the 1010 bp Eco RI-Xba I fragment. The resulting vector, designated Zem238, contains a Kpn I site after the finger domain. Zem238 was digested with Bgl II and Kpn I, gel purified to remove the wild-type finger domain, and ligated with each of the eight consensus sequences to generate expression vectors 238-Fcon 1 to 238-Fcon 8.

Example 5

Site-Specific Mutagenesis of the Activation Site

For site-specific mutagenesis, a 472 bp Eco RI fragment comprising the t-IDA sequence from bp 802 to bp 1274 was isolated from Zem99 and cloned into the Eco RI site of M13mp18 (replicative form). The recombinant phage were transfected into E. coli JM101, and anti-sense strand DNA was isolated.

Site-specific mutagenesis was then carried out on the single-stranded anti-sense template DNA using one of the mutagenic primers shown in Table 4 and ZC87 (5' TCC CAG TCA CGA CGT $^3$') as second primer. Oligonucleotides ZC487, 488, 489 and 620 change the Phe at position 274 to Glu, Gly, Arg or Pro, respectively. Oligonucleotides ZC797, 874, 1013 and 1027 change the Arg at position 275 to Gly, Leu, Pro or Asp, respectively. Oligonucleotide 621 introduces a Leu in place of the Lys at position 277. Oligonucleotide 928 changes the Ile at position 276 to Pro. Oligonucleotide 875 changes Arg (275) to Leu and oligonucleotide 927 changes Phe (274) to Pro in the mutant which previously had Lys (277) converted to Leu. Thus, oligonucleotides 875 and 927 can be used to generate double mutations. Twenty pmoles of phosphorylated mutagenic primer and 20 pmoles of the second primer were combined with one pmole of single-stranded template in 10 μl of 20 mM Tris pH 7.5, 10 mM MgCl$_2$, 50 mM NaCl, 1 mM DTT and the mixture was incubated at 65° C. for 10 minutes, then 5 minutes at room temperature, and placed on ice. Ten μl of 20 mM Tris pH 7.5, 10 mM MgCl$_2$, 2 mM ATP, 10 mM DTT containing 1 mM dNTPs, 2.5 units DNA polymerase I (Klenow fragment), and 3.5 units DNA ligase were added to the annealed DNA, and the mixture was incubated 3 hours at 15° C. The DNA was then transfected into competent *E. coli JM*101, and the cells were plated on YT agar and incubated at 37° C. The DNA was then transferred to nitrocellulose and prehybridized at the Tm-4° C. of the mutagenic primer for 1 hour in 6× SSC, 10× Denhardt's and hybridized to $^{32}$p-labeled mutagenic primer at Tm-4° C. in the same solution. After three washes at Tm-4° C., filters were exposed to X-Fay film overnight. Additional wash steps were performed at 5° C. higher increments as necessary to identify mutant plaques. The mutated inserts were sequenced by the dideoxy method.

TABLE 4

ZC463 5'CCT CAG TTT AAA ATC AAA3'
ZC487 5'CAG CCT CAG GAG CGC ATC AAA3'
ZC488 5'CAG CCT CAA GGT CGC ATC AAA3'
ZC489 5'CAG CCT CAG AGA CGC ATC AAA3'
ZC620 5'CAG CCT CAG CCT CGC ATC AA3'
ZC621 5'TTT CGC ATC CTC GGA GGG CTC3'
ZC797 5'CTT CAG TTC GGC ATC AAA3'
ZC814 5'G CCT CAG TTC GGC ATC AAA GG3'
ZC874 5'CT CAG TTT CTC ATC AAA GG3'
ZC875 5'CT CAG TTT CTC ATC CTC GG3'
ZC927 5'CAG CCT CAG CCT CGC ATC CT3'
ZC928 5'CAG TTT CGC CCC AAA GGA GG3'
ZC1013 5'CT CAG TTT CCC ATC AAA GG3'
ZC1027 5'CCT CAG TTT GAC ATC AAA GG3'

Figure 13:
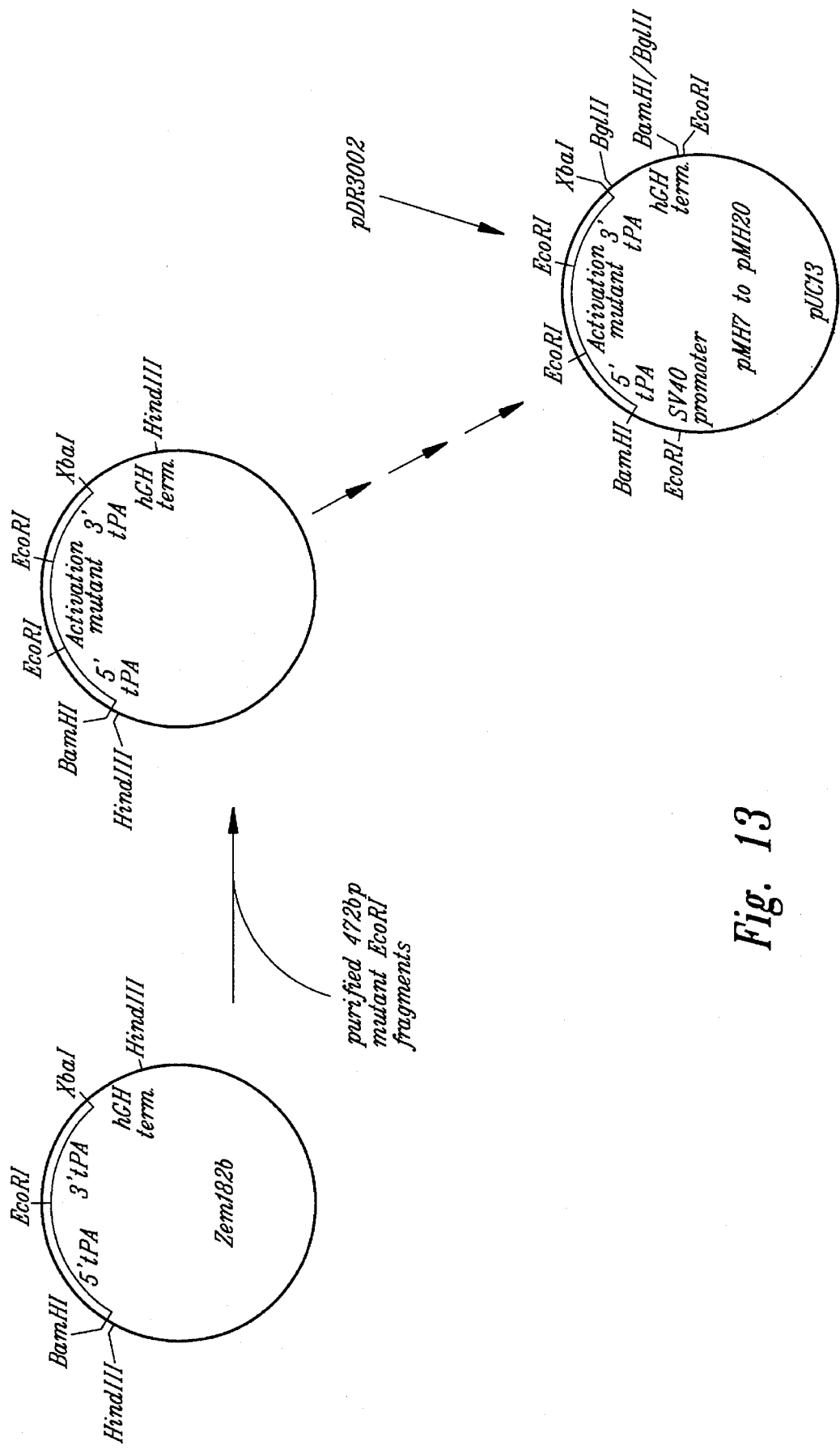
FIG. 13 illustrates the construction of the pMH series of plasmids, comprising mutant DNA sequences encoding t-PA derivatives with altered cleavage sites.

Expression vectors for the altered sequences were then constructed (FIG. 13). The sequence just upstream of the ATG start codon of the t-PA sequence in Zem94 was then prepared by site-specific mutagenesis, resulting in the positioning of Hind III and Bam HI sites adjacent to the ATG. The resultant nucleotide sequence contains an adenine in the -3 position. Single-stranded M13 template DNA was prepared by inserting a ~800 bp Hind III-Eco RI fragment from Zem94, comprising polylinker, pre-pro, and a portion of the mature t-PA sequences, into M13mp19. Site-specific mutagenesis was carried out essentially as described above using the oligonucleotide ZC444 (5'CAT CCA TGG TGG ATC CAA GCT TGG C3') as mutagenic primer. The mutated inserts were sequenced by the dideoxy method, and a clone was selected in which polylinker sequences had been deleted and the Bam HI site at the 5' end of the pre-pro sequence had been restored. This phage clone was digested with Bam HI and Eco RI, and the 5' t-PA sequence was isolated. Zem99 was digested with Eco RI, and the fragment comprising the 3' portion of the t-PA sequence and the hGH terminator was isolated. The two fragments were then joined with Bam HI+Eco RI-digested pIC19H (Marsh et al., *Gene* 32: 481–486, 1984) in a three-part ligation. A plasmid containing the t-PA fragments in the proper orientation was selected and designated Zem182. Plasmid Zem182 was partially digested with Eco RI, and the ends were filled using DNA polymerase I (Klenow fragment). The fragment was gel-purified and recircularized using T$_4$ DNA ligase. A plasmid in which the Eco RI site at the 3' end of the hGH terminator was destroyed was selected and designated Zem182b.

The vector pDR3002 was used for expression of the above-described sequences. Plasmid Zem86 (described in Example 1) was digested with Hind III and the ends filled in using DNA polymerase I (Klenow fragment). The linearized DNA was then digested with Eco RI and a ~350 bp fragment, comprising the SV40 ori sequence, was gel-purified and ligated to Sma I+Eco RI-digested pUC13. The resultant vector was designated pDR3001. Plasmid pDR3001 was digested with Sal I and Eco RI and the ~350 bp fragment, comprising SV40 ori and polylinker sequences, was gel-purified. Zem86 was partially digested with Eco RI and completely digested with Xho I to remove the SV40 ori sequence. The SV40 fragment from pDR3001 was then joined to the linearized Zem86. The resultant plasmid was designated pDR3002 (FIG. 13).

Replicative form (RF) DNA was prepared from the mutagenized phage, and the modified t-PA sequences were purified as Eco RI fragments. Plasmid Zem182b was digested with Eco RI, the vector sequences containing the 5' and 3' portions of the t-PA coding sequence were treated with calf alkaline phosphatase, and the modified t-PA sequences were inserted. The resultant plasmids were digested with Bam HI and Xba I, and the t-PA fragments were inserted into Bam HI+ Xba I-cut pDR3002. The resultant vectors were designated pMH7 through pMH20 (Table 5 and FIG. 13).

TABLE 5

| Protein | Sequence of Amino Acids 273–279 |
|---------|--------------------------------|
| Native t-PA | Gln—Phe—Arg—Ile—Lys—Gly—Gly |
| pMH7 | Gln—Gly—Arg—Ile—Lys—Gly—Gly |
| pMH8 | Gln—Phe—Arg—Ile—Leu—Gly—Gly |
| pMH9 | Gln—Arg—Arg—Ile—Lys—Gly—Gly |
| pMH10 | Gln—Pro—Arg—Ile—Lys—Gly—Gly |
| pMH11 | Gln—Glu—Arg—Ile—Lys—Gly—Gly |
| pMH12 | Gln—Phe—Lys—Ile—Lys—Gly—Gly |
| pMH13 | Gln—Phe—Gly—Ile—Lys—Gly—Gly |
| pMH14 | Gln—Pro—Arg—Ile—Leu—Gly—Gly |
| pMH15 | Gln—Phe—Leu—Ile—Lys—Gly—Gly |
| pMH16 | Gln—Phe—Leu—Ile—Leu—Gly—Gly |
| pMH17 | Gln—Phe—Arg—Pro—Lys—Gly—Gly |
| pMH18 | Gln—Phe—Pro—Ile—Lys—Gly—Gly |
| pMH19 | Gln—Phe—Asp—Ile—Lys—Gly—Gly |
| pMH20 | Gln—Phe—Gly—Ile—Leu—Gly—Gly |

A second construct encoding t-PA with the Pro substitution at amino acid 276 was made as follows. M13tg130W template (Example 2) was annealed to a mutagenic oligonucleotide (5'GAG CCC TCC CTT TGG GCG AAA CTG AGG C3'). Mutagenesis was carried out essentially as described in Example 2. Mutant plaques were screened and sequenced to identify clones having the desired mutation. One such clone and its encoded protein were designated #2550.

Example 6

Mutagenesis of the Growth Factor Region and K1 Glycosylation Site

The growth factor region of t-PA encompasses a highly conserved, triple-disulfide bonded structural domain which may be responsible for several functional activities. These activities include a role in the rapid clearance of t-PA from plasma and a receptor-like activity. To alter these activities in order to enhance the fibrinolytic activity and specificity of the molecule, the t-PA sequence was modified by site-specific mutagenesis. In order to facilitate this mutagenesis, the t-PA coding sequence was modified to introduce unique restriction enzyme sites at regions flanking certain structural domains.

Figure 14:
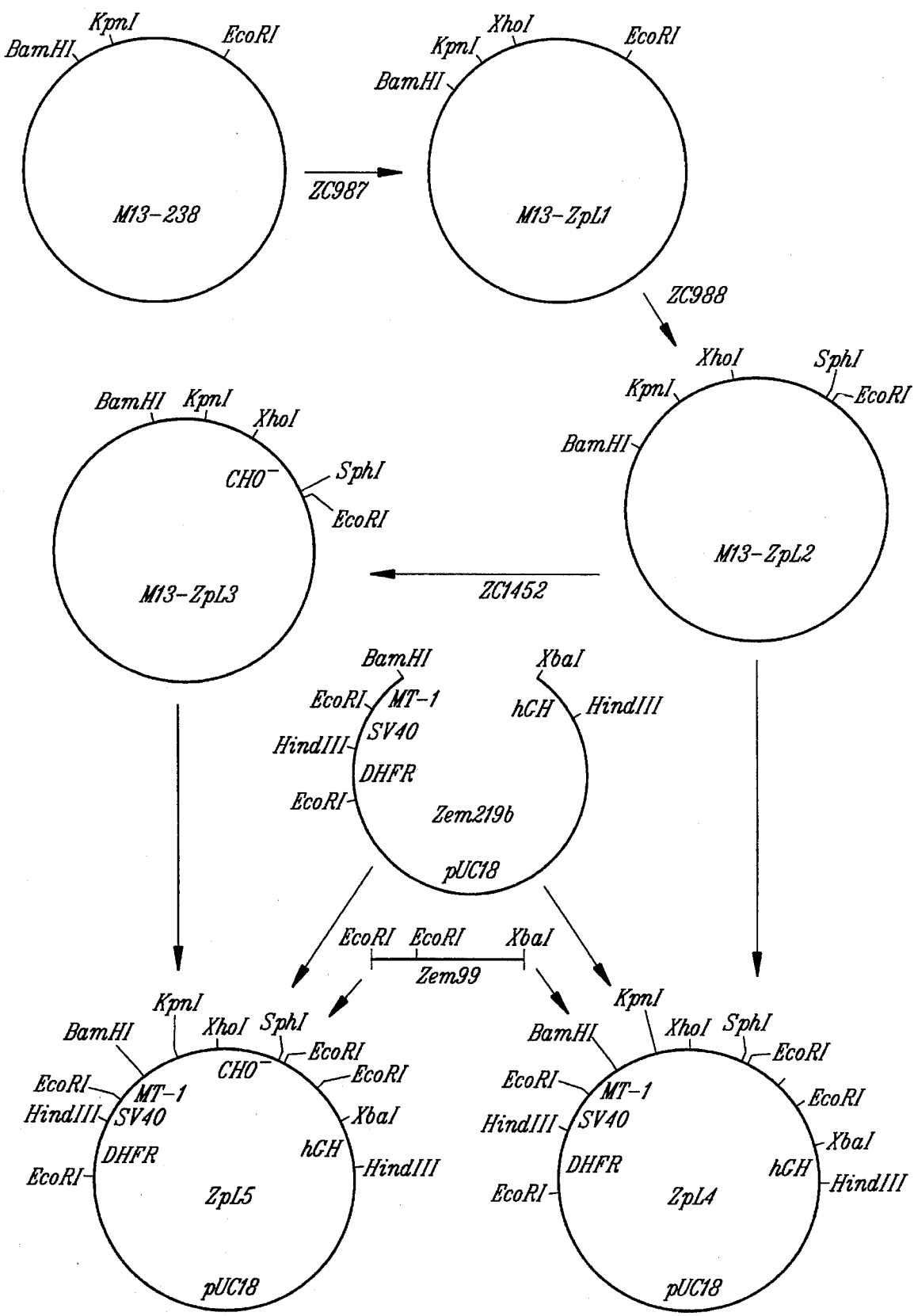
FIG. 14 illustrates the construction of vectors used to express DNA sequences encoding t-PA derivatives having modified growth factor domains.

The mutagenized Bam HI-Eco RI t-PA fragment in M13 described in example 4 was further mutagenized using a template prepared by PEG precipitation of the phage supernatant followed by phenol/chloroform extraction and ethanol precipitation. One ug of this DNA was hybridized with 10 ug of oligonucleotide ZC987 (5'CAC GTG GCT CGA GTA TCT ATT TC3') to introduce an Xho I site at the 3' end of the growth factor (GF) domain. The mixture was boiled briefly, incubated at 65° C. for 5 minutes, and the temperature brought slowly down to 4° C. before adding 10 ul of 0.2M HEPES pH7.8, 2 ul of 100 mM DTT, 1 ul of 1M MgCl$_2$, 20 ul of 2.5 mM each dNTP, 10 ul of 10 mM ATP, 2.5 units of DNA polymerase I (Klenow fragment) and 2 units of T4 DNA ligase, final volume adjusted to 100 ul with H$_2$O. After extension at 37° C. for 2 hours, the DNA was transfected into competent *E. coli* JM101 cells. The plates were screened by hybridization and after sequence confirmation of the mutagenesis, the new construction (ZpL1) was used to prepare template for a second mutagenesis. Oligonucleotide Zc988 (5' CTC AGA GCA TGC AGG GG 3') was used to introduce an Sph I site at the 3' end of the first kringle domain. Sequence confirmation of this mutagenesis resulted in a t-PA fragment, designated ZpL2, which was subsequently used for further mutagenesis using ZC1452 (5' CAA CGC GCT AGA TTG CCA GTT GGT 3') to eliminate the carbohydrate addition site in the kringle 1 domain. Confirmation of this mutagenesis resulted in the M13 phage clone ZpL3 (FIG. 14).

For insertion or substitution of growth factor region sequences within the complete t-PA DNA sequence, the Bam HI to Eco RI fragments from ZpL2 and ZpL3 (replicative form) were isolated and used in ligation reactions containing the partial Eco RI to Xba I 3' t-PA fragment from plasmid Zem99 and Bam HI, Xba 1 cut expression vector Zem219. FIG. 14 shows the expression plasmids ZpL4, containing the wild-type t-PA construction, and ZpL5, containing the carbohydrate minus construction.

Plasmids ZpL4 and ZpL5 were further modified by replacing portions of the growth factor domain coding sequence. Amino acid substitutions were designed with the goal of disrupting possible specific receptor interactions without drastically altering the chemical nature of the GF domain. Oligonucleotides (shown in Table 6) encoding the growth factor region replacement domains shown in FIG. 15 were synthesized. The initial four replacement fragments (FIG. 15) were generated from 14 different oligonucleotides and represent only a subset of mutants that can be made by ligating together groups of six of the illustrated oligonucleotides. Fragment A results in the replacement of t-PA amino acids 63–70 with a consensus receptor binding region, Fragment B results in the substitution of t-PA amino acids 52–91 with the entire growth factor region of human factor IX, Fragment C results in the replacement of t-PA amino acids 52–55 with the corresponding 4 amino acids from factor IX and Fragment D results in the replacement of t-PA amino acids 52–70 with a consensus growth factor region. The consensus growth factor sequence represents a sequence that is weighted toward the natural t-PA sequence at positions where there is no clear consensus amino acid or where the consensus amino acid would drastically alter the chemical nature of the exposed region. In fragments A, C and D the Cys corresponding to amino amino acid 83 in native t-PA has been changed to Ser. Oligonucleotides were kinased and simultaneously labeled to a low specific activity with $^{32}$p-ATP. Appropriate groups of 6 oligonucleotides were mixed with DNA ligase and after 1 hour at 37° C. the products were sorted on a 6% polyacrylamide-8M urea sequencing gel. The bands corresponding to DNA fragments coding for full-length growth factor domains were cut out and the DNA was eluted in 2.5M ammonium acetate. The DNA was ethanol precipitated and resuspended in water to a concentration of 1 pmole/ul. RF DNA was prepared from constructions ZpL2 and ZpL3 (described above) and digested with Kpn I and Xho I. The linearized vectors were ligated with the purified mutant growth factor domain sequences. After screening by sequencing, each of the four mutant growth factor domains was isolated as a Bam HI to Xho I fragment and ligated to vectors ZpL4 or ZpL5 which had been previously digested with Bam HI and Xho I and purified away from the wild-type growth factor coding region. The resultant expression vectors ZpL4A to D and ZpL5A to D are used to transfect tk–BHK cells by the electropotation method. High producer cell lines are isolated and the proteins are purified and characterized for plasma half-life and fibrin binding characteristics.

TABLE 6

| ZC1351 | | | | | | | 27 | | | | | |
|---|---|---|---|---|---|---|---|---|---|---|---|---|
| CTG | TTA | AAT | CTT | GTT | CTC | AAC | CTA | GAT | GTT | TTA | ATG | GAG | GA |
| ZC1352 | | | | | | | 27 | | | | | |
| ATT | AAA | ACA | TCT | AGG | TTC | AGA | ACA | AGA | TTT | AAC | AGG | TAC | |
| ZC1353 | | | | | | | 27 | | | | | |
| ACA | TGC | ATG | GAA | GGA | AAT | CAT | CTT | GCT | AAT | TTT | GTT | TGT | CAA | TGT |
| CCT | | | | | | | | | | | | | |
| ZC1354 | | | | | | | 27 | | | | | |
| TTG | ACA | AAC | AAA | ATT | AGC | AAG | ATG | ATT | TCC | TTC | CAT | GCA | TGT | TCC |
| TCC | | | | | | | | | | | | | |
| ZC1355 | | | | | | | 27 | | | | | |
| GAA | GGA | TTT | GCT | GGA | AAA | TCT | TGT | GAA | ATT | GAT | AC | | |
| ZC1356 | | | | | | | 27 | | | | | |
| TCG | AGT | ATC | AAT | TTC | ACA | AGA | TTT | TCC | AGC | AAA | TCC | TTC | AGG | ACA |
| ZC1357 | | | | | | | 27 | | | | | |
| CTG | TTA | AAT | CTT | GTG | AAT | CTA | ATC | CTT | GTC | TTA | ATG | GAG | GA |
| ZC1358 | | | | | | | 27 | | | | | |
| ATT | AAG | ACA | AGG | ATT | AGA | TTC | ACA | AGA | TTT | AAC | AGG | TAC | |
| ZC1359 | | | | | | | 27 | | | | | |
| TCT | TGT | AAA | GAT | GAT | ATT | AAT | TCA | TAT | CAA | TGT | TGG | TGT | CCT |
| ZC1360 | | | | | | | 27 | | | | | |
| CCA | ACA | TTC | ATA | TGA | ATT | AAT | ATC | ATC | TTT | ACA | AGA | TCC | TCC |
| ZC1361 | | | | | | | 27 | | | | | |
| TTT | GGA | TTT | GAA | GGA | AAA | AAT | TGT | GAA | ATT | GAT | AC | | |
| ZC1362 | | | | | | | 27 | | | | | |
| TCG | AGT | ATC | AAT | TTC | ACA | ATT | TTT | TCC | TTC | AAA | TCC | AAA | AGG | ACA |

TABLE 6-continued

| | | | | | | | | 27 | | | | | | |
|---|---|---|---|---|---|---|---|---|---|---|---|---|---|---|
| ZC1363 ACA CCT | TGT | CAA | CAA | GCT | CTT | TAT | TTT | TCT | GAT | TTT | GTT | TGT | CAA | TGT |
| ZC1364 TTG TCC | ACA | AAC | AAA | ATC | AGA | AAA | ATA | AAG | AGC | TTG | TTG | ACA | TGT | TCC |

Example 7

Substitution of Set for Cys (84)

The t-PA coding sequence in Zem99 was mutagenized to encode a serine at position 84 (amino acid numbers refer to the sequence shown in FIG. 1). Zem99 was digested with Bam HI, and a 2.4 kb fragment comprising the t-PA coding sequence and the hGH terminator was isolated. This fragment was joined to Bam HI-digested M13mp18 (obtained from Pharmacia), and the resultant recombinant phage was used to transfect *E. coli* JM103. A phage clone having the desired insertion was designated M13mp18/Bam-Zem99.

The t-PA DNA sequence was mutagenized to encode serine at amino acid 84 by means of site-specific mutagenesis using the oligonucleotide 5' CCT GGT ATC GAT TTC ACT GCA CTT CCC 3'. The oligonucleotide was annealed to M13mp18/Bam-Zem99 and mutagenesis was carried out using standard procedures. Single-stranded mutagenized phage were sequenced and a clone having the desired sequence alteration was selected. Replicative form DNA was prepared (designated M13-9200RF) and digested with Bgl II and Hind III. The 2.3 kb t-PA fragment was isolated and joined to the Bgl II+Hind III–cut Zem99. The resultant vector was designated Zem99-9200.

An *E. coli* RR1 transformant containing plasmid Zem99-9200 has been deposited with FRI under Accession No. FERM P-9274.

Example 8

Construction of a Representative Hybrid DNA and Expression in Transfected Mammalian Cells Two machine-synthesized oligonucleotides (Table 7) were used to construct the coding sequence for the first twelve amino acids of the amino terminus of $\alpha_2$-PI. FIG. 16 illustrates the amino-terminal amino acid sequence of a hybrid plasminogen activator containing this peptide.

TABLE 7

| | |
|---|---|
| ZC1185 | 5' GA TCC TTT TAA ACC TGT TAA CGG AGA AAC TTG TTC TTG ATT A 3' |
| ZC1186 | 5' GA TCT AAT CAA GAA CAA GTT TCT CCG TTA ACA GGT TTA AAA G 3' |

100 ng of each oligonucleotide (30 ng/ul) were combined with 12 ul of $H_2O$, 2 ul of 10×kinase buffer (50 mM Tris pH 7.5, 100 mM $MgCl_2$, 50 mM dithiothreitol, 1 mM EDTA), 2 ul of 10 mM ATP and 1 ul of T4 DNA kinase (10 U/ul). The mixture was incubated at 37° C. for 30 minutes, then at 65° C. for 10 minutes, and frozen at −20° C.

Two ug of Bgl II-digested plasmid Zem99 were incubated for one hour at 37° C. in the presence of 2 units of calf alkaline phosphatase. The reaction mixture was extracted with phenol:$CHCl_3$ (1:1) and the DNA was precipitated with ethanol. The precipitate was dissolved on 50 ul of TE buffer (10 mM Tris pH 8.0, 1 mM EDTA).

The complete coding sequence for the hybrid protein was then constructed. 40 ng of cleaved and phosphatased Zem99 were combined with 0.5 ng each of kinased ZC1185 and ZC1186 in 1× ligase buffer containing 1 mM ATP and 2 units of T4 DNA ligase in a final volume of 20 ul. The reaction mixture was incubated at 15° C. for 16 hours, then used to transform competent *E. coli* HB101 cells. DNA was prepared from transformants and screened for the presence of Bgl II, Dra I and Hpa I restriction sites to determine the orientation and number of oligonucleotide insertions. A clone having the desired pattern of restriction sites was sequenced to confirm the presence of the desired fusion.

The Zem99-derived plasmid containing the oligonucleotide insert was digested with Bam HI and Xba I and the entire coding sequence for the hybrid protein was recovered as a ca. 2000 bp fragment. This fragment was then ligated to Zem219b, which had been linearized by digestion with Bam HI and XbaI. The resultant plasmid was designated 219b/$\alpha_2$-PI.

Plasmid 219b/$\alpha_2$-PI was used to transfect tk⁻BHK cells by electropotation. Stably transfected cells were selected with 250 nM methotrexate. Colonies were screened by immunofilter assay using an adaptation of the method of McCracken, et al. (*Biotechniques*, March/April 1984, 82–86). Briefly, nitrocellulose filters (Millipore HATF 08250 or 13750) were pre-wet in serum-free medium and placed on the plates over Teflon® mesh (Spectrum Medical Industries, Inc., Los Angeles, Calif.) and the plates were incubated at 37° C. for 1–4 hours. Filters were removed from the plates, placed in Buffer A (50 mM Tris pH 7.4, 5 mM EDTA, 0.05% NP-40, 150 mM NaCl, 01.25% gelatin), and developed by conventional western blotting procedure (Towbin, et al., *Proc. Natl. Acad. Sci. USA* 76: 4350, 1979) using an anti-t-PA antibody. Several positive colonies were selected for further characterization. The highest producing clone was grown in large-scale culture. Four 15 cm confluent plates were cultured in Dulbecco's MEM containing 1% fetal calf serum, 1% PSN (Gibco Laboratories, Grand Island, N.Y.), 2 mM L-glutamine and 1000 U/ml aprotinin. The hybrid protein was affinity purified using a monoclonal antibody to native t-PA linked to CNBr-activated Sepharose 4B.

Example 9

Characterization of Representative Hybrid Protein

The sequence of the first 15 amino-terminal residues of the purified hybrid protein were determined by Edman degradation. Results were in agreement with the sequence predicted from the hybrid DNA sequence (FIG. 16).

The hybrid protein was then tested for its ability to cross link with fibrin in a covalent manner. The hybrid protein and native t-PA were labeled with $125_I$ using Iodobeads (Pierce Chemical Co., Rockford, Ill.). Normal human plasma was clotted in the presence of the labeled protein by adding thrombin and either 50 mM $CaCl_2$ or 50 mM EDTA (Factor XIIIa requires $Ca^{++}$ for activity). The resulting clot was separated from the serum by centrifugation, washed, and dissolved in 10% SDS, 10% 2-mercaptoethanol, 4M urea by boiling for 20 minutes, and the solution was electrophoresed on an SDS-polyacrylamide gel and subjected to autoradiography. The position of the labelled plasminogen activator on the gel was diagnostic for cross linking. The hybrid protein was shown to be covalently cross linked to the clot in the presence, but not in the absence, of $Ca^{++}$. Native t-PA was not cross linked under either condition.

A second series of experiments was performed to examine the dependence of cross linking on factor XIIIa. Results, shown in Table 8, confirmed that factor XIIIa was needed to catalyze the cross linking of the hybrid protein to fibrin.

TABLE 8

| Protein | Conditions | Cross-Linking |
|---|---|---|
| native t-PA | thrombin + $Ca^{++}$ | – |
|  | thrombin + $Ca^{++}$ + FXIII | +/– |
|  | thrombin + EDTA + FXIII | – |
| $\alpha_2$-PI/t-PA | thrombin + $Ca^{++}$ | – |
|  | thrombin + $CA^{++}$ + FXIII | +++ |
|  | thrombin + EDTA + FXIII | – |

From the foregoing it will be appreciated that, although specific embodiments of the invention have been described herein for purposes of illustration, various modifications may be made without deviating from the spirit and scope of the invention. Accordingly, the invention is not to be limited except as by the appended claims.

We claim:

1. A hybrid plasminogen activator comprising a human tissue plasminogen activator or a variant thereof having one or more amino acid substitutions within the cleavage site sequence Gln-Phe-Arg-Ile-Lys-Gly-Gly, and an amino-terminal cross-linking domain, wherein the cross-linking domain comprises the amino terminal twelve amino acids of $\alpha_2$-plasmin inhibitor.

2. A hybrid plasminogen activator having the sequence Ser-Asn-Gln-Glu-Glm-Val-Ser-Pro-Leu-Thr-Gly-Leu-Lys-Gly-Ser-tPA, wherein tPA is human tissue plasminogen activator or a variant thereof having one or more amino acid substitutions within the cleavage site sequence Gln-Phe-Arg-Ile-Lys-Gly-Gly.

3. The plasminogen activator of claim 1 wherein the Arg residue in the cleavage site sequence is replaced with a Gly residue.

4. The plasminogen activator of claim 1 wherein said activator contains a thrombin cleavage site between the fibrin-binding domain and the serine protease domain.

5. The plasminogen activator of claim 4 wherein the Phe residue in the cleavage site sequence is replaced with a Pro residue.

6. A pharmaceutical composition comprising a plasminogen activator according to claim 1 in combination with a physiologically acceptable carrier or diluent.

7. The composition of claim 6 wherein said carrier or diluent is sterile water or sterile saline.

* * * * *